United States Patent
Soto, Sr. et al.

(10) Patent No.: US 9,657,298 B2
(45) Date of Patent: May 23, 2017

(54) RECOMBINANT NITROGEN-FIXING BACTERIAL STRAIN, INOCULUM CONTAINING THE SAME AND APPLICATION METHODS

(71) Applicants: CONSEJO NACIONAL DE INVESTIGACIONES CIENTIFICAS Y TECNICAS (CONICET), Buenos Aires (AR); INSTITUTO NACIONAL DE TECNOLOGIA AGROPECUARIA (INTA), Buenos Aires (AR); INIS BIOTECH LLC, Milford (DE)

(72) Inventors: Gabriela Cynthia Soto, Sr., Prov. de Buenos Aires (AR); Nicolas Daniel Ayub, Prov. de Buenos Aires (AR); Lorena Maria Setten, Prov. de Bunos Aires (AR)

(73) Assignees: CONSEJO NACIONAL DE INVESTIGACIONES CIENTIFICAS Y TECNICAS (CONICET), Buenos Aires (AR); INSTITUTO NACIONAL DE TECNOLOGIA AGROPECUARIA (INTA), Buenos Aires (AR); INIS BIOTECH LLC, Milford, DE (US)

( * ) Notice: Subject to any disclaimer, the term of this patent is extended or adjusted under 35 U.S.C. 154(b) by 0 days.

(21) Appl. No.: 14/360,054

(22) PCT Filed: Nov. 22, 2012

(86) PCT No.: PCT/IB2012/056643
§ 371 (c)(1),
(2) Date: May 22, 2014

(87) PCT Pub. No.: WO2013/076687
PCT Pub. Date: May 30, 2013

(65) Prior Publication Data
US 2014/0336050 A1 Nov. 13, 2014

(30) Foreign Application Priority Data
Nov. 24, 2011 (AR) .......................... P20110104381

(51) Int. Cl.
| | | |
|---|---|---|
| A01N 63/00 | (2006.01) |
| C12N 1/20 | (2006.01) |
| C12P 19/34 | (2006.01) |
| C07H 21/04 | (2006.01) |
| C12N 15/78 | (2006.01) |
| C07K 14/21 | (2006.01) |
| C12N 9/02 | (2006.01) |
| C12R 1/39 | (2006.01) |

(52) U.S. Cl.
CPC ............. *C12N 15/78* (2013.01); *A01N 63/00* (2013.01); *C07K 14/21* (2013.01); *C12N 9/0095* (2013.01); *C12N 9/0097* (2013.01); *C12R 1/39* (2013.01)

(58) Field of Classification Search
CPC .......... C12R 1/39; C07K 14/21; C12N 15/78; C12N 9/0097; C12N 9/0095; A01N 63/00
USPC ..... 504/117; 435/252.34, 252.3, 252.4, 91.1; 536/23.1, 23.2
See application file for complete search history.

(56) References Cited

U.S. PATENT DOCUMENTS 7,485,426 B2 * 2/2009 Harney ................. C07H 21/00
435/254.2

FOREIGN PATENT DOCUMENTS

CN 102041241 A 5/2011

OTHER PUBLICATIONS

Broun et al., Catalytic plasticity of fatty acid modification enzymes underlying chemical diversity of plant lipids. Science, 1998, vol. 282: 1315-1317.*
Devos et al., Practical limits of function prediction. Proteins: Structure, Function, and Genetics. 2000, vol. 41: 98-107.*
Elo et al., Humus bacteria of Norway spruce stands: plant growth promoting properties and birch, red fescue and alder colonizing capacity. FEMS Microbiol., Ecol., 2000, vol. 31: 143-152.*
Garcia et al., Effects of inoculation with plant growth promoting rhizobacteria (PGPRs) and Sinorhizobium fredii on biolgical nitrogen fixation, nodulation and growth of Glycine max cv. Osumi. Plant and Soil., 2004, vol. 267: 143-153.*
Kisselev L., Polypeptide release factors in prokaryotes and eukaryotes: same function, different structure. Structure, 2002, vol. 10: 8-9.*
Quaglitto et al., Three native Pseudomonas fluorescens strains tested under growth chamber and field conditions as biocontrol agents against damping-off in alfalfa. Biol. Cont., 2009, vol. 51: 42-50.*
Seffernick et al., Melamine deaminase and Atrazine chlorohydrolase: 98 percent identical but functionally different. J. Bacteriol., 2001, vol. 183 (8): 2405-2410.*
van Loon LC., Plant responses to plant growth-promoting rhizobacteria. Eur. J. Plant. Pathol., 2007, vol. 119: 243-254.*
Whisstock et al., Prediction of protein function from protein sequence. Q. Rev. Biophysics., 2003, vol. 36 (3): 307-340.*
Witkowski et al., Conversion of b-ketoacyl synthase to a Malonyl Decarboxylase by replacement of the active cysteine with glutamine. Biochemistry, 1999, vol. 38: 11643-11650.*
Yan et al., Nitrogen fixation island and rhizosphere competence traits in the genome of root-asscociated Pseudomonas stutzer. A1501. PNAS., 2008, vol. 105 (21): 7564-7569.*

(Continued)

*Primary Examiner* — Ganapathirama Raghu
(74) *Attorney, Agent, or Firm* — Young & Thompson

(57) ABSTRACT

Recombinant bacterial strains comprising heterologous nif genes in its genome, and capable of fixing nitrogen. The strain may be, for example, a recombinant *Pseudomonas fluorescens* strain comprising heterologous nif genes in its genome. An inoculum and a method for increasing plant productivity are further described.

6 Claims, 6 Drawing Sheets

(56) References Cited

OTHER PUBLICATIONS

Wilson et al., Release of recombinant microorganisms. Annu. Rev. Microbiol., 1993, vol. 47: 913-944.*
International Search Report PCT/IB2012/056643 dated May 31, 2013.
Max Mergeay et al: "'F'-plasmid transfer from *Escherichia coli* to Pseudomonas fluorescens", Journal of Bacteriology, American Society for Microbiology, Washington, DC; US, vol. 135, No. 1, Jul. 1, 1978, pp. 18-28, XP009147350.
V. Krishnapillai et al: "Expression of Klebsiella his and nif Genes in Serratia marcescens, Erwinia herbicola and Proteus mirabilis", Archives of Microbiology, Springer, DE, vol. 127, No. 2, Sep. 1, 1980, pp. 115-118, XP008162120.
Yan Yongliang et al: "Global transcriptional analysis of nitrogen fixation and ammonium repression in root-associated Pseudomonas stutzeri A1501", BMC Genomics, vol. 11, Jan. 2010, XP002697187.
Chinese Office Action dated Apr. 27, 2015; Application No. 201280064329.3.

* cited by examiner

RECOMBINANT NITROGEN-FIXING BACTERIAL STRAIN, INOCULUM CONTAINING THE SAME AND APPLICATION METHODS

This application refers to recombinant nitrogen-fixing bacterial strains, the inoculum containing the same and application methods. More specifically, it refers to a recombinant bacterial strain comprising heterologous nif genes and capable of nitrogen fixation.

BACKGROUND

Two treatments/technologies have been described which are aimed at improving productivity in respect of plants grown in nitrogen-deficient soil: (a) the fertilization with nitrogenous compounds (e.g., urea) and (b) the inoculation with nitrogen-fixing bacteria. There exist two types of nitrogen-fixing bacteria: (b1) symbiotic bacteria which fix nitrogen in association with leguminous plants (e.g., *Rhizobium* sp. and *Sinorhizobium* sp.) and (b2) free-living nitrogen-fixing bacteria (e.g., *Azospirillum brasilense* and *Azotobacter vinelandii*). The first type was successfully employed to improve productivity in respect of crops grown in soils poor in nitrogen, but it is only applicable to leguminous plants. The second type could be employed with all kinds of plants (not only in respect of leguminous ones). However, it has not yet been stated that the nitrogen fixed by these bacteria is sufficient to overcome the nitrogen deficiency suffered by plants grown in soils poor in nitrogen. Despite this, species such as *A. brasilense* and *A. vinelandii* are currently employed in the formulation of inoculants since such bacteria produce phytohormones capable of stimulating root development. This is a feature of agronomic importance, but it bears no relation to the nitrogen-fixation ability of these bacteria.

The patent publication EP0108508 describes *Escherichia coli* strains modified with genes related to nitrogen fixation. However, the *E. coli* strains are not employed to improve productivity in respect of plants grown in soils poor in nitrogen, but in order to transfer the nitrogen-fixation ability to other microorganisms, such as *Rhizobium japonicum*.

BRIEF DESCRIPTION OF THE INVENTION

One of the subject matters of this invention is to provide a bacterial strain, for example, recombinant *Pseudomonas fluorescens* comprising nif genes. Such strain will be capable of fixing nitrogen and has been transformed with cosmid X940. In a preferred embodiment, the recombinant strain comprises from PST_1302 to PST_1306 (SEQ ID NO: 5) and from PST_1313 to PST_1359 genes (SEQ ID NO: 6); from PST_1307 to PST_1312 genes are deleted and instead, a kanamycin resistance gene from plasmid pUC4K (X06404) has been inserted. In a preferred embodiment, the recombinant *Pseudomonas fluorescens* strain comprises from PST_1302 to PST_1306 (SEQ ID NO: 5) and from PST_1313 to PST_1359 (SEQ ID NO: 6) genes and a kanamycin resistance gene. It is evident for the experts that on the basis of the examples provided, any person can obtain different nitrogen-fixing bacterial strains and species from strains which do not fix nitrogen by employing the microorganisms transformation and construction techniques described herein. Therefore, any bacterial strain or species transformed with heterologous nif genes which develops the ability to fix nitrogen falls within the scope of this invention. The nif genes can be any of those known and disclosed, for example from PST_1302 to PST_1306 (SEQ ID NO: 5) and from PST_1313 to PST_1359 (SEQ ID NO: 6) genes. Based on what can be learnt from this application, such genes can be introduced into bacteria which do not fix nitrogen and transform them into nitrogen-fixing bacteria, which are additionally efficient to improve plant productivity.

Another subject matter of this invention is to provide an inoculum aimed at improving plant productivity which contains a recombinant bacterium, for example, *Pseudomonas fluorescens*, with such strain comprising heterologous nif genes, and a vehicle. The inoculum may comprise between $8.10^8$-$2.10^9$ cells/ml. Based on what can be learnt from the examples provided, experts can prepare different inoculants by employing the invention recombinant bacteria, all of the inoculants falling within the scope of this invention.

Another subject matter of this invention is to provide a method to improve nitrogen fixation in plants which entails applying an amount comprised between $1.6 \; 10^8$ and $4 \; 10^8$ of recombinant bacteria, for example, *Pseudomonas fluorescens*, to the soil, with such bacteria containing heterologous nif genes. In a preferred embodiment, the recombinant bacterial strain comprises from PST_1302 to PST_1306 and from PST_1313 to PST_1359 genes, whereas genes from PST_1307 to PST_1312 are deleted and instead, a kanamycin resistance gene has been inserted, for example, the resistance gene from plasmid pUC4K (X06404). The plant can be any known one, for example, a monocotyledon or a dicotyledon. In a preferred embodiment, the method comprises the application to the soil of an amount comprised between $1.6 \; 10^8$ and $4 \; 10^8$ of recombinant bacteria, for example, recombinant *Pseudomonas fluorescens*, per liter of soil volume. As it can be observed, the method is applicable to any kind of plant and soil poor in nitrogen.

DETAILED DESCRIPTION OF THE INVENTION

The recombinant nitrogen-fixing bacterial strain which is the object of this invention entails a quality leap forward in technology. The applicant has no knowledge of any technologies aimed at obtaining microorganisms which can develop an ability to fix nitrogen by means of repeatable, efficient techniques such as genetic engineering and transformation. The availability of the invention inoculum boosts the field of the inoculants aimed at solving the problem posed by the limited availability of nitrogen in the soil since not only does it employ natural bacterial isolations (nonrecombinant bacteria) but also recombinant bacteria transformed with nif genes which fix nitrogen, such as bacteria transformed with from PST 1302 to PST 1306 (SEQ ID NO: 5) and from PST 1313 to PST 1359 (SEQ ID NO: 6) genes of *Pseudomonas stutzeri* A1501.

A bacterial strain, for example recombinant *Pseudomonas fluorescens* comprising nif genes of, for instance, the *Pseudomonas stutzeri* A1501 strain, has been prepared, with such recombinant strain being capable of fixing nitrogen when transformed with cosmid X940, which carries nif genes. In a preferred embodiment, the strain comprises from PST_1302 to PST_1306 and from PST_1313 to PST_1359 genes of *Pseudomonas stutzeri* A1501. The transformed strain was termed Pf-5X940.

The invention delivers important quantitative results since the inoculation with Pf-5X940 caused an increase of over 200% in productivity in respect of plants grown in soils poor in nitrogen, whereas the inoculation with *Azotobacter vinelandii* BMN0359 (a type strain of the *Azotobacter vinelandii* species, which fixes nitrogen and was provided by the National Bank of Microorganisms of the Agronomy School of the University of Buenos Aires) did not produce significant variations, thus maintaining consistency with the null/low efficiency of natural bacteria (those not transformed) when fixing important amounts of nitrogen as free-living bacteria.

Figure 1:
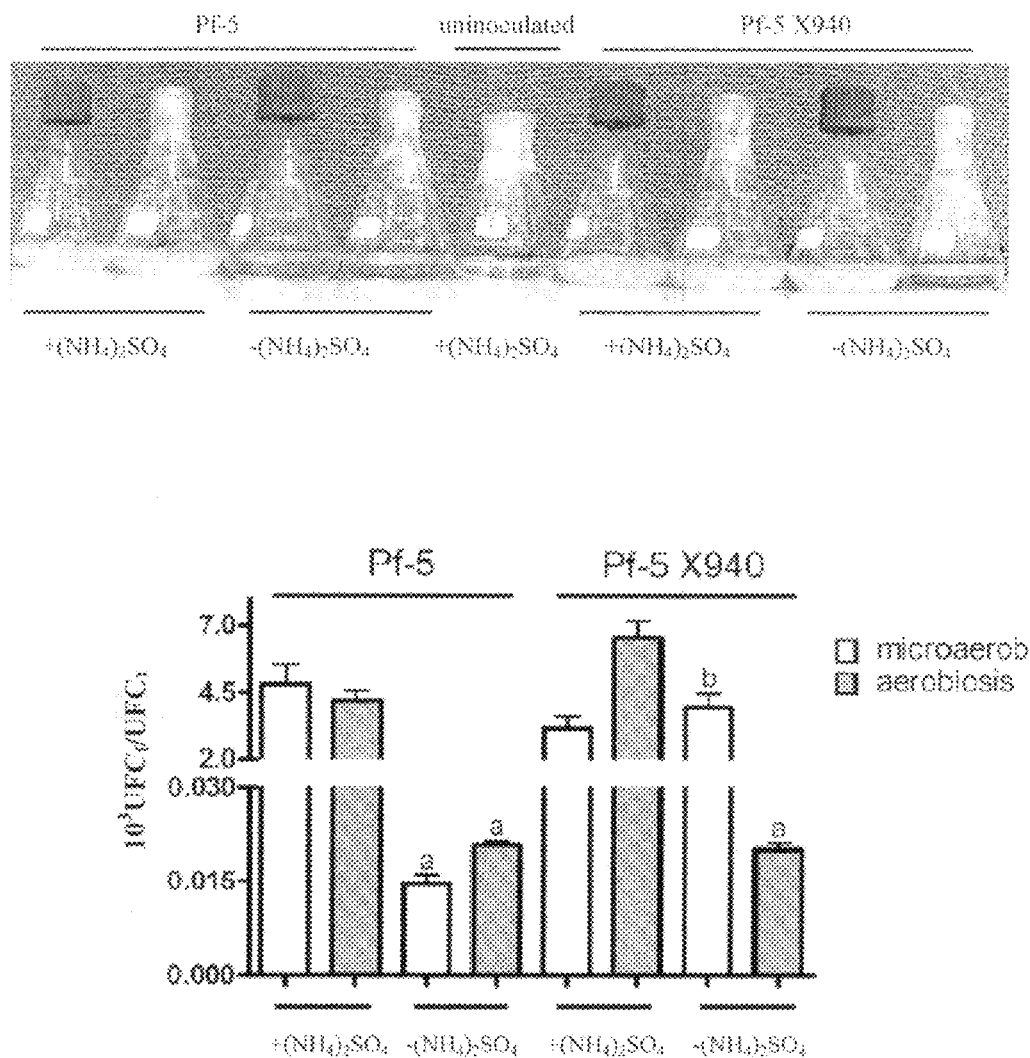
FIG. 1 shows the effect of the transformation of *Pseudomonas* Pf-5 with cosmid X940. The covered Erlenmeyer flasks simulate microaerobiosis conditions and the Parafilm-sealed Erlenmeyer flasks simulate aerobiosis conditions. The statistical analysis employed was ANOVA, followed by Tukey contrasts. The letters refer to the comparative treatments. The same letters refer to not statistically significant differences. a and b showed significant differences with $p < 0.01$.

The growth of wild bacteria (Pf-5) and recombinant bacteria (Pf-5X940) was assessed during a period of 48 hours in L medium (a semisynthetic medium) without nitrogen (−(NH$_4$)$_2$SO$_4$) or a nitrogen-supplemented medium (+(NH$_4$)$_2$SO$_4$), subject to aerobiosis or microaerobiosis under laboratory conditions (FIG. 1). In the course of the first 24 hours, only the nitrogen-supplemented cultures grew, whereas after a period of 48 hours, there was also a considerable growth in the Pf-5X940 bacteria in L medium without nitrogen under microaerobiosis conditions (FIG. 1). 1). The recombinant bacteria did not show signs of growth in L medium without nitrogen under aerobiosis conditions, thus suggesting that the heterologous nitrogenase complex is atmospheric-oxygen sensitive. This is not strange since it is known that autologous nitrogenase complexes are irreversibly inhibited in contact with gaseous oxygen (Biochemistry 1994, 33:389-397).

The growth of the Pf-5X940 recombinant bacteria in L medium without nitrogen under microaerobiosis conditions was quantified through colony forming units count (FIG. 1). In L medium without nitrogen under microaerobiosis conditions, only one duplication of the amount of bacteria in the Pf-5 culture (≈1 generation) could be observed, whereas the Pf-5X940 culture evidenced an increase in the amount of bacteria of over three levels (≈12 generations) (FIG. 1). Thus, FIG. 1 shows that the transformation with cosmid X940 confers the Pf-5 bacterium the ability to fix nitrogen, and consequently, the capacity to grow without an organic and/or inorganic source of nitrogen.

Figure 2:
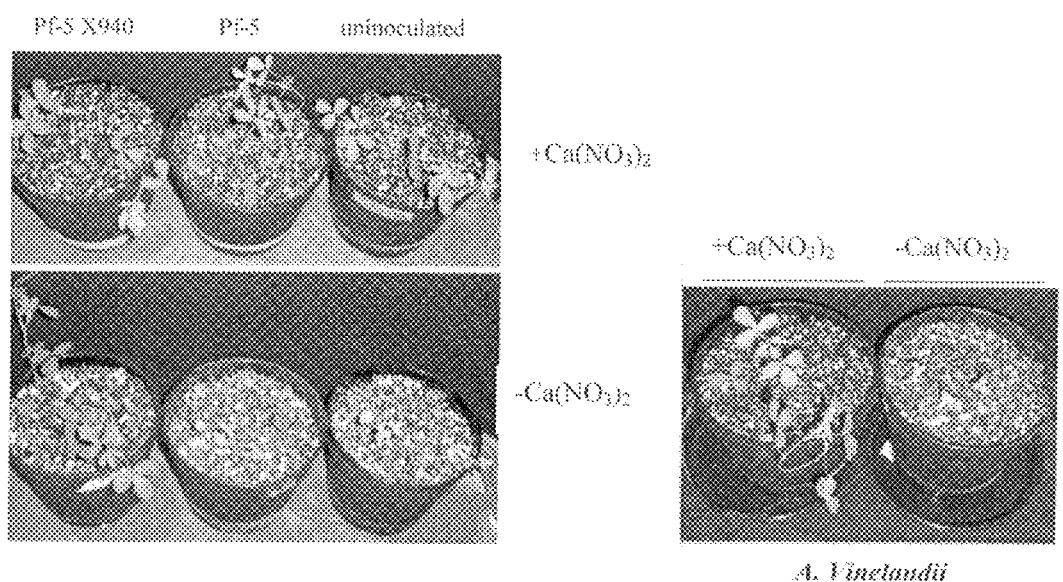
FIG. 2 shows the effect of the inoculation with Pf-5 X940 on the growth of alfalfa plants in presence or absence of nitrogen in the substrate. The statistical analysis employed was ANOVA, followed by Tukey contrasts. The comparisons were made between plants which received the same inoculation treatment under different nitrogen conditions in the substrate. $p < 0.01$ and *$p < 0.001$.
Figure 2:
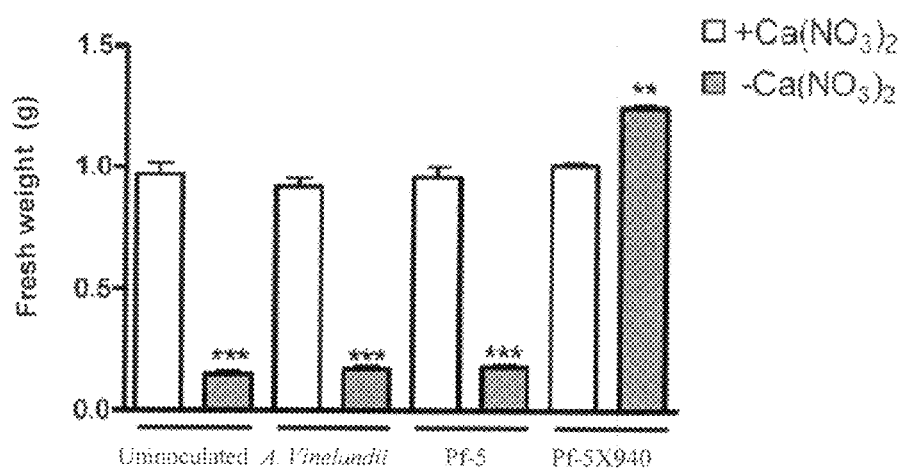
Figure 3:
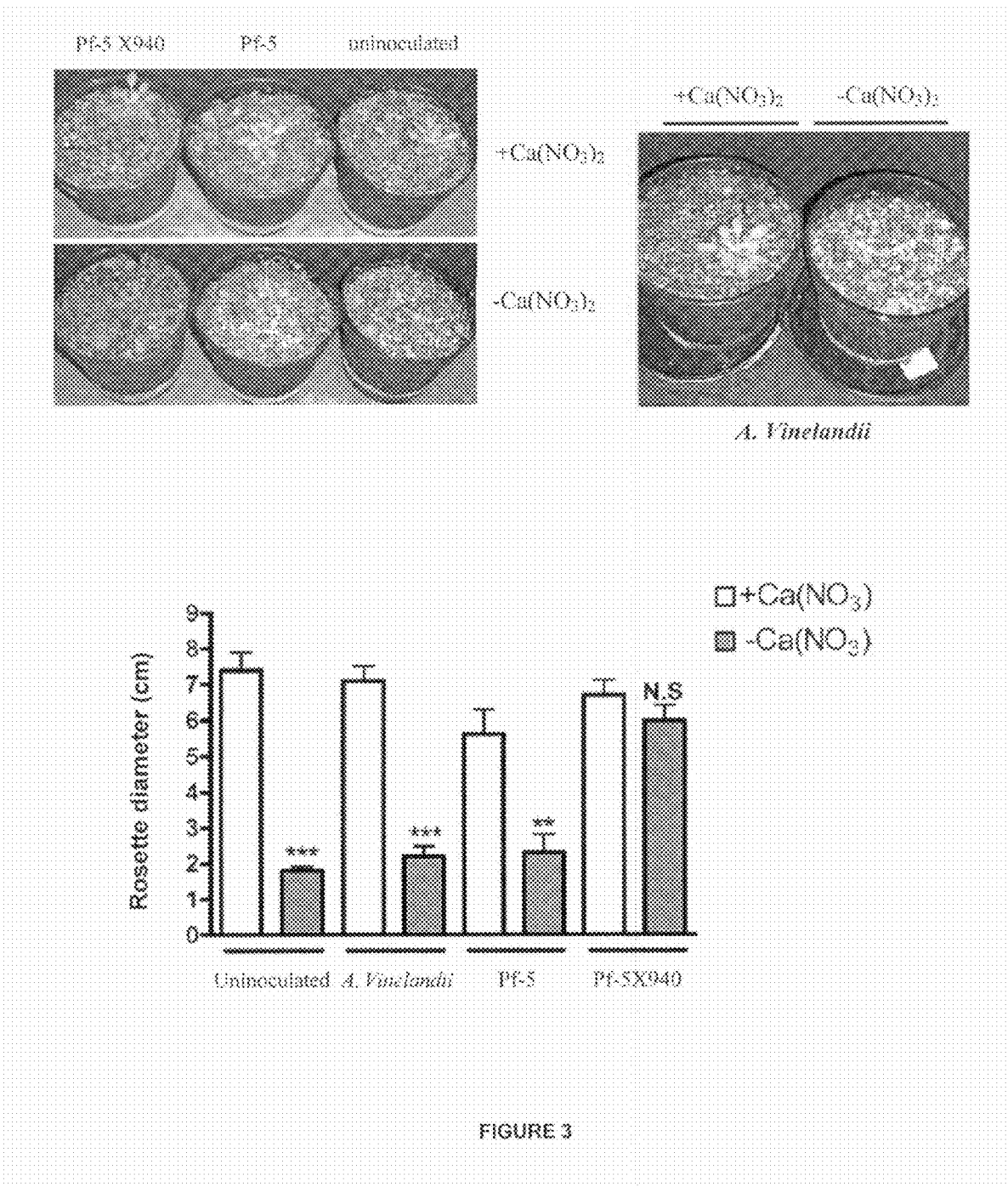
FIG. 3 shows the effect of the inoculation with Pf-5 X940 on the size of an *Arabidopsis* rosette in presence or absence of nitrogen in the substrate. The statistical analysis employed was ANOVA, followed by Tukey contrasts. The comparisons were made between plants which received the same inoculation treatment under different nitrogen conditions in the substrate. $p < 0.01$ and *$p < 0.001$., N.S.: not significant.
Figure 4:
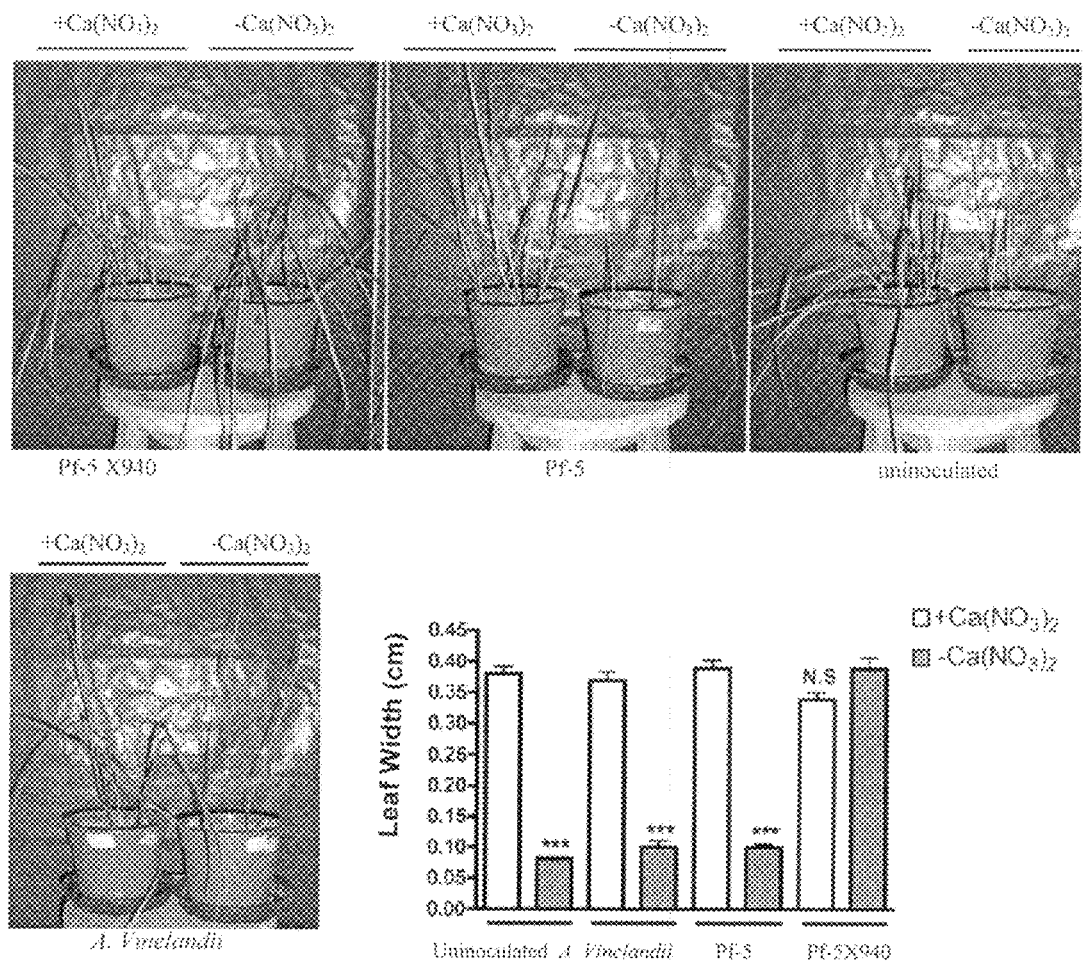
FIG. 4 shows the effect of the inoculation with Pf-5 X940 on the width of the first leaf of Tall Fescue in presence or absence of nitrogen in the substrate. The statistical analysis employed was ANOVA, followed by Tukey contrasts. The comparisons were made between plants which received the same inoculation treatment under different nitrogen conditions in the substrate. p<0.01 and *p<0.001., N.S.: not significant.

An assessment was conducted in respect of the effect of the inoculation with Pf-5, Pf-5X940 and *Azotobacter vinelandii* BMN0359 on the growth of three plants belonging to the two most important plant groups at agronomic and economic level: the dicotyledons Alfalfa (FIG. 2) and *Arabidopsis* (FIG. 3) and the monocotyledon Fescue (FIG. 4). These three plants were grown as a part of a hydroponic system and watered with a minimum medium referred to as "INTA13" without nitrogen (−Ca(NO$_3$)$_2$) or a nitrogen-supplemented medium (+Ca(NO$_3$)$_2$), with Pf-5, Pf-5 X940 or *Azotobacter vinelandii* BMN0359 inoculums, or without an inoculum (control). After 40 days of growth, the plants which were not inoculated or were inoculated with the Pf-5 and BMN0359 wild bacteria showed a significantly lower productivity in the medium referred to as INTA13 without nitrogen in comparison with this same medium when supplemented with nitrogen (FIG. 2, FIG. 3 and FIG. 4). This productivity deficiency in the nitrogen-free medium was completely overcome by the inoculation with the Pf-5X940 recombinant bacterium (FIG. 2, FIG. 3 and FIG. 4). In fact, the productivity of the Alfalfa plant inoculated with Pf-5X940 and grown in the nitrogen-free medium referred to as INTA13 was significantly higher than the productivity observed in respect of this plant when not inoculated or inoculated with wild bacteria grown in a nitrogen-supplemented INTA13 (FIG. 2). FIGS. 2, 3 and 4 show that inoculation with Pf-5 X940 constitutes an effective method to improve productivity in respect of plants grown under nitrogen-limited conditions.

This invention is further illustrated by means of the following examples, which are not intended to limit the scope thereof. Therefore, it must be clearly understood that other embodiments, modifications and equivalents of the present invention can be resorted to if, after reading this description, they would be suggested to those skilled in the art as long as they do not depart from the spirit of this invention and/or scope of the attached claims.

EXAMPLES

Example 1: Construction of Recombinant Bacteria of the Invention

Two 255 bp segments of PST_1306-PST_1307 and PST_1312-PST_1313 intergenic regions of (CP000304) *Pseudomonas stutzeri* A1501 were obtained through PCR using the following primers:

```
SEQ ID N° 1:
5'-CGGGATCCCCGAATAGAGGTCTGTCCCCG 3'

SEQ ID N° 2:
5'-CGGGATCCCCGGGGCGCTGGTGC3'

SEQ ID N° 3:
5'-CGGTCGACTCGGTGCGGCGCTCG3'-

SEQ ID N° 4:
5'-CGGTCGACGCCAAGGCCGCCCGC 3',
``` where the BamHI and SalI restriction sites have been underlined, respectively. The PCR cycle used for both amplification reactions was the following: 3 minutes at 94° C. (201.2° F.); 34 cycles of 45 seconds at 94° C. (201.2° F.)—30 seconds at 50° C. (122° F.)—30 seconds at 72° C. (161.6° F.) and 10 minutes at 72° C. (161.1° F.). The amplification segment corresponding to the PST_1306-PST_1307 intergenic region was digested with BamHI and bound to a kenamycin resistance gene obtained from the plasmid pUC4K (X06404) digested with BamHI, resulting in Plasmid A. The amplification segment corresponding to the PST_1312-PST_1313 intergenic region was digested with SalI and cloned within Plasmid A digested with SalI, resulting in Plasmid B. As it is based in plasmid pUC4K which does not replicate in *Pseudomonas* (Ayub et al., *Extremophiles* 2009 13(1):59-66), Plasmid B is a suicide vector for bacteria belonging to genus *Pseudomonas*. *Pseudomonas stutzeri* A1510 competent cells were transformed with Plasmid B by electroporation according to the protocol described hereinbelow. The bacteria were cultivated in 25 ml of LB in 125 ml Erlenmeyer flasks at 28° C. (82.4° F.) with stirring at 250 rpm during a period of 16 hours. 1.5 ml of this culture was taken and centrifuged at 16,000 g during 1 minute at 25° C. (77° F.). Then, the bacterial pellet was washed three times in 1 ml of a 310 mM sucrose solution and resuspended in 100 µl of a 300 mM sucrose solution. These 100 µl of resuspended bacteria have from $10^9$ to $10^{10}$ bacterial cells according to the CFU/ml measurement. For the electroporation, 0.5 µg of Plasmid B was used un 100 µl of resuspended bacteria, with the later application of the following pulses (25 AF, 200 V, 2.5 kV). Then, 1 ml of LB was added to the transformed cells and it was incubated in a 2 ml-volume Eppendorf tube with light stirring (at 100 rpm) during a period of 3 hours at 25° C. (77° F.). Then, the transformed bacteria were selected in LB agar containing 50 µg/ml of kanamycin. A kanamycin resistance colony (clone) was selected and termed A1501C. This strain was able to fix nitrogen when growing in an L medium without nitrogen, i.e., without the addition of $(NH4)_2SO_4$.

Figure 5:
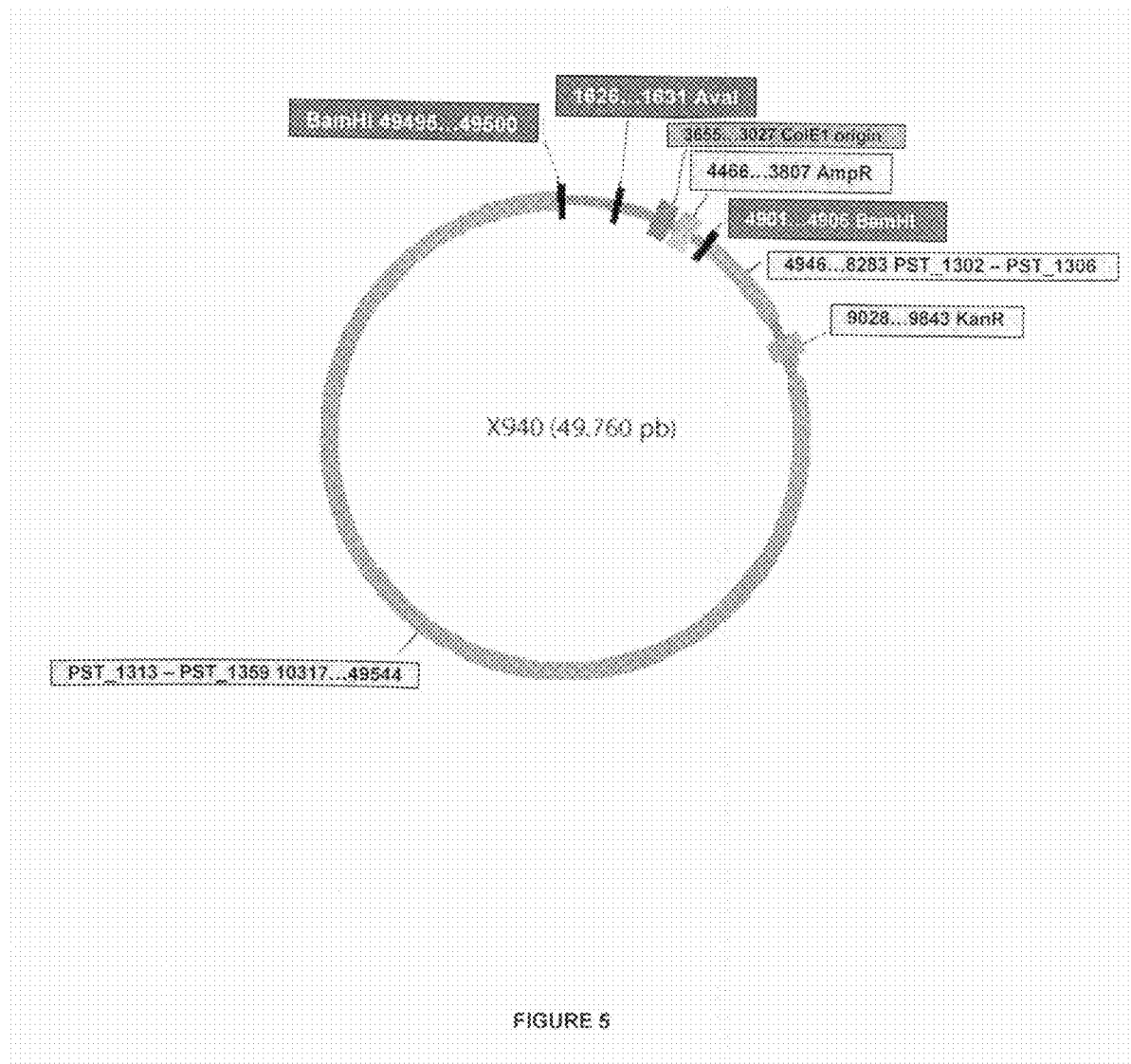
FIG. 5 shows a representation of cosmid X940.
Figure 6:
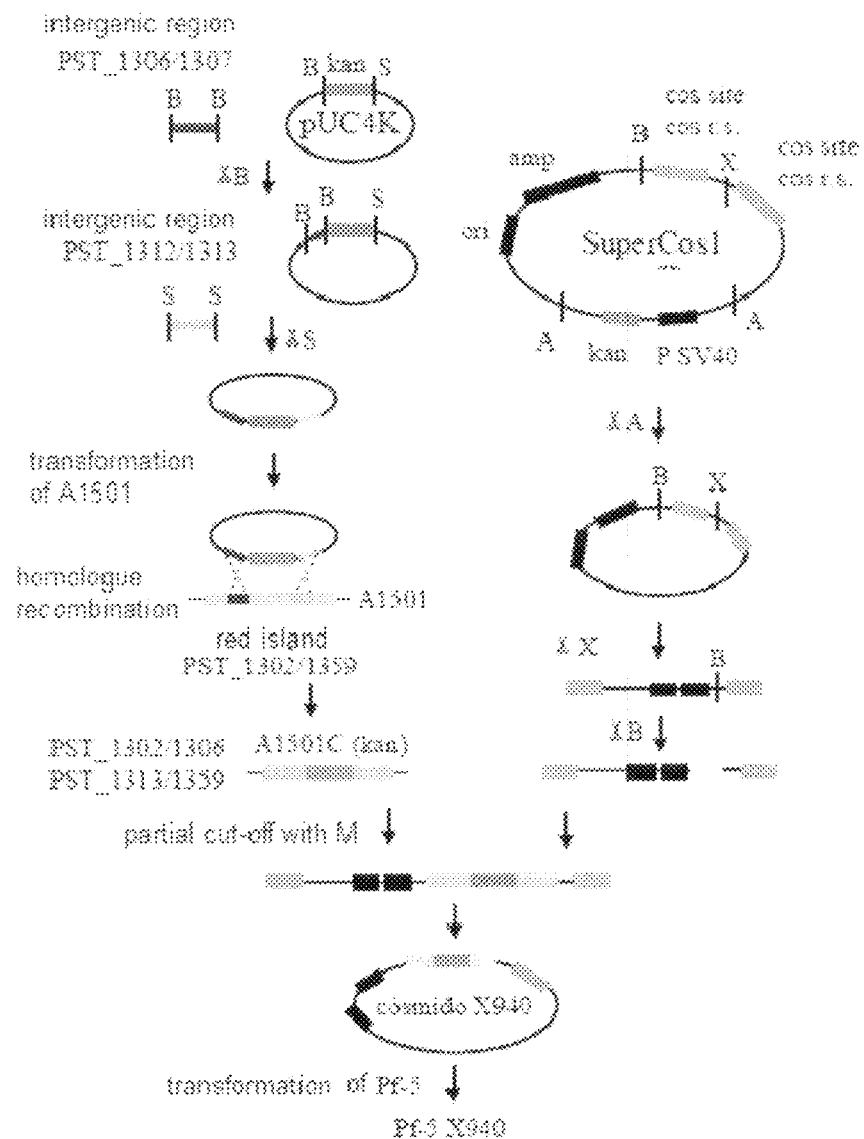
FIG. 6 shows the process of construction of cosmid X940 in a diagram. B: BamHI, S: SalI and M: MboI.

The SuperCos1 cosmid (M99566.1) (vector) was digested with AvaI and rebound with the purpose of eliminating its kanamycin resistance region (neoR reporter cassette) resulting in a recombinant vector termed C. Then, vector C was digested with BamHI and XbaI, and bound to segments of genomic DNA of A1501C bacteria digested with MboI obtained through a genomic library of A1501C in *Escherichia coli*. Then, a 50 µg/ml kanamycin and 100 µg/ml ampicillin resistance clone was searched and found within such library. The isolated recombinant cosmid of this strain was termed X940 (FIG. 5) and the sequencing thereof by primer walking confirmed the presence of A1501 bacteria nif genes. The cosmid X940 was introduced by transformation in cells composing Pf-5 *Pseudomonas fluorescens* using the same electroporation protocol described in the previous paragraph for A1501 *Pseudomonas stutzeri*. The transformed bacteria were selected in LB agar with 50 µg/ml of kanamycin. The Pf-5 *Pseudomonas fluorescens* recombinant bacteria containing the cosmid X940 was termed "Pf-5 X940". FIG. 6 shows a drawing of the whole cosmid X940 construction process and the procurement of the transformed strain of the invention termed "Pf-5 X940".

Example 2: Bacteria Growth Conditions

The cultures were made in 125 ml Erlenmeyer flasks containing 25 ml of incubated L medium at 28° C. (82.4° F.) with stirring at 300 rpm. The L medium was prepared according to the following formula: 1 g $KH_2PO_4$, 3 g $K_2HPO_4$, 0.1 g NaCl, 0.5 g $(NH4)_2SO_4$, 0.25 g $MgSO_4$ $7H_2O$, 1 mg $FeCl_3$ $6H_2O$, 0.017 mg $CuCl_2$ $2H_2O$, 0.029 mg $ZnSO_4$ $7H_2O$, 0.144 mg $MnCl_2H_2O$, 0.147 mg $CaCl_2$ $2H_2O$, 0.005 mg $NaMoO_4$, 1 g citric acid, 5 g glucose, 100 mg yeast extract, 1 L, pH=7. Two aeration conditions termed aerobiosis (Erlenmeyer flasks covered with Parafilm) and microaerobiosis (Erlenmeyer flasks covered with a screw lid) were used. In order to assess the growth in limiting nitrogen conditions, the L medium was used but without the addition of nitrogen, i.e. without the addition of $(NH4)_2SO_4$. The cultures started from an optical density of 0.05-580 nm. The pre-cultures used to make the cultures were performed under the same conditions as the culture (25 ml of L medium in 125 ml Erlenmeyer flasks, at 28° C. (82.4° F.), at 300 rpm) with an incubation period of 24 hours. The pre-cultures were delivered from LB agar plates. Before inoculating the cultures, the pre-cultures were washed twice in an L medium without nitrogen (speed: 16,000 g, period: 1 minute) to dismiss a nitrogen supply from the pre-culture to the culture. The bacterial culture growth was assessed using optical density measurements at 580 nm and through a colony forming unit count per milliliter of culture (CFU/ml) during a period of 48 hours.

Example 3: Preparation of the Inoculum

The cultures were made in 125 ml Erlenmeyer flasks containing 25 ml of incubated L medium at 28° C. (82.4° F.) with stirring at 300 rpm during a period of 24 hours from LB agar plates. The culture was centrifuged at 10,000 g during a period of 5 minutes and it was resuspended in 25 ml of physiological saline (FS: 9 g NaCl/l). Then, the amount of bacteria present in these resuspended cultures was assessed, which resulted in the following value range: $8.10^8$-$2.10^9$ CFU/ml. Each pot of 1 liter volume was inoculated with 0.2 ml of resuspended culture.

Example 4: Inoculation Essays

To perform the inoculation essays, Columbia-0 *Arabidopsis thaliana*, *Schenodorus arundinaceus* (Festuca Alta Gentos) and *Medicago sativa* (Alfalfa GAPP 969) seeds were sterilized and vernalized during a period of 5 days at 4° C. in the darkness. Then, the plants were chamber incubated at 23° C. under a photoperiod of 16 h light/8 h dark, with a light intensity of 150 µmol $m^{-2}$ $sec^{-1}$, under hydroponics conditions characterized by a peat, perlite and vermiculite mixture (1:1:1 v/v), a perlite and vermiculite mixture (1:1 v/v) or 100% vermiculite, respectively. The plants were let grow in INTA13 medium (0.13 g $CaCl_2$ $2H_2O$, 0.25 g $MgSO_4$ $7H_2O$, 0.14 g $Na_2HPO_4$, 0.1 g $KH_2PO_4$, 1 mg $Na_2MoO_4$ $2H_2O$, 0.6 mg $MnSO_4H_2O$, 1 mg $CuSO_4$ $5H_2O$, 1 mg $ZnSO_4$ $7H_2O$, 1 mg $H_3BO_3$, 4 mg $FeCl_3$ $6H_2O$, 1 L, pH=6.5) with or without 0.24 g/L $Ca(NO_3)_2$ $4H_2O$ as nitrogen source during a period of 40 days.

Both pots and pot plates were sterilized with 70% ethanol. The substrates used as support (peat, perlite and vermiculite) were heat sterilized (at 350° C. during a period of 30 minutes), and then washed twice with sterile distilled water to remove residual salts. The inoculation with bacteria (Pf-5, Pf-5 X940 and *Azotobacter vinelandii* BMN0359) was performed immediately after the vernalization, as described hereinbelow. An overnight 25 ml bacteria culture grown at 28° C. (82.4° F.) in L medium was taken and then centrifuged; the pellet was resuspended in 25 ml of physiological saline. Then, 200 µl of this bacterial suspension were used (from $1.6\ 10^8$ to $4\ 10^8$ bacteria) to inoculate each pot of 1 liter volume.

SEQUENCE LISTING

<160> NUMBER OF SEQ ID NOS: 6

<210> SEQ ID NO 1
<211> LENGTH: 29
<212> TYPE: DNA
<213> ORGANISM: Artificial Sequence
<220> FEATURE:
<223> OTHER INFORMATION: primer 1

<400> SEQUENCE: 1
cgggatcccc gaatagaggt ctgtccccg                              29

<210> SEQ ID NO 2
<211> LENGTH: 23
<212> TYPE: DNA
<213> ORGANISM: Artificial Sequence
<220> FEATURE:
<223> OTHER INFORMATION: primer 2

<400> SEQUENCE: 2
cgggatcccc ggggcgctgg tgc                                    23

<210> SEQ ID NO 3
<211> LENGTH: 23
<212> TYPE: DNA
<213> ORGANISM: Artificial Sequence
<220> FEATURE:
<223> OTHER INFORMATION: primer 3

<400> SEQUENCE: 3
cggtcgactc ggtgcggcgc tcg                                    23

<210> SEQ ID NO 4
<211> LENGTH: 23
<212> TYPE: DNA
<213> ORGANISM: Artificial Sequence
<220> FEATURE:
<223> OTHER INFORMATION: primer 4

<400> SEQUENCE: 4
cggtcgacgc caaggccgcc cgc                                    23

<210> SEQ ID NO 5
<211> LENGTH: 3338
<212> TYPE: DNA
<213> ORGANISM: Pseudomonas stutzeri

<400> SEQUENCE: 5
ctagctttcc gccgcaagtg cggcatcgag tcgcgccacc aggctgccgt cggcttccag    60
gccgaggatg atgtcgcaac cgccgaccag ctcgccacgc aggaacagct gcgggtaggt   120
cggccactgc gagatcttcg gcagcttctc gcggatatgc ggtgccagta gcacgttgac   180
cgtggcgaac ggccggccgc tgttcttcaa tgcctccacc gcggcgcggg agaaaccgca   240
ctccggcacg cccggcgtgc ccttcatgta cagcagcacc ggatgctcgg cgagttgctg   300
gcgtatgcgt gcttcggtat cgagaacttg catgcgttca ctccattgcc agggtgcagg   360
gggagttgta ggcgcagggg ctggcatggg cccgctgtgg gcgatccttc caggcctcgt   420
agccgccgtc caggctgtag caattgatga agccgaaatc gctgaacagc tgtgccatgt   480
cacggctggc atgaccgtgc tcgcaacaga tgatcagatg gacgtgattt ggcgtgctct   540
tgagcagcgt gcgcaagttc agctcgctga ggcgggtggc gcgcgggtca tggccctggc   600
agtaggcgcg ggcatcgcgc atgtccagca gcatggtgtt ttcggtcgcc aacagccgct   660

```
gggcctgctc gacgctgatg cgttggtagt cgctcattgc tcttctccaa aacaatcgtg    720
ataggtcggg caggcttcac aagaggggga gcggcatacg tagccgccgt cctgttcgca    780
tagttgtttg tagaggaact tcttccagcg catgtcctgg gtattgcgcc gggccagctg    840
cgggaagttg tgcatcagca gcgcgtacag ctgcgcccgc gaggccaggc cgaggtcgcg    900
ccacaggtgt tcgccaccga ggcaggcggc agcgacgatg gctgccatcg ccggttcgcc    960
gtggtcgtcc tggccgccca gcagcaggtc gtgcagcgcc tgccattctt cccggcgcag   1020
cgccagcaac tcttcgcgca aggcgtcgcg ctcgccgagc aaggcctcgt cggcgctacg   1080
ggatggtggt cgcagcccat ggcgcgtcag gagctcggcg tactgcgccg cgtcgagccc   1140
gaggtgctgc ggcaggcaac tacggccttc gcgctgggcg cggatgatct gcgctagcca   1200
ggccgggttg tcgttgactg cgacctccag gcacaacgcg gcccggctca ttgcggcgtg   1260
ctcgcggcgg ggctgcaacc gagcaccgag ctggtgccca gcaacagcc gctgatgctc    1320 ggtgccagcg ctggcagccg gcctttgcac ggcagccagg cattgatgcc gaccaggtcg   1380
aagtcgacca tgtagtgcat gccgcagcgg atcagcgggc ggcggatcaa cagcggctgg   1440
gccaccatca gctccagtgc ctgttcggcg ctcagttcgc tgacatccag ctcgccgtac   1500
ttgatcgccg gggccgacgg gttgaaccac tcggccaccg gcagccggcc gaagaacggc   1560
cgcaggcgtt ccggcgtcca ggcctcgcgc agcaggtcgc gcacttccag ctcgatgccc   1620
gctgaacgca gcagctcctt ctgcaggcgg ttggtggcgc aaccgggctt ctcgtagaag   1680
atgatgcagg acatgcaac ctcctcaacg ggcctggatg gcgcgcatgg cctcggccaa    1740
ccgctccggc ggaatgcccg tcagcgagcc ggctgggttg gccgggctgc cgtcggcgag   1800
caggatcgcg ccttcgatgg ggcagatgct cgcgcactgt tgctcggcgt agtcgccatc   1860
gcattcggtg cacttgtgcg cgctgatgcg gaagtacgca gtgccggggc tgatcgcctc   1920
gctcgggcag acgtccacgc aggcccagca gttgacgcag gattcgacga tttgcagtgc   1980
catactccac ctcctcatgc catcaggcat tgctccgctg cgcccaccga cgcatcgaga   2040
cggccattgg cgatcatttc ctggtacacc tccagcacgg cttcctcgat gggctccatg   2100
gcgtgctcgc cattgggctg gatgccgcg gcttccagct cgcccagggg ttcgaagccg    2160
atcttcgagc agagcaccgc ctcgcagccc ttgagcgcgc ggatgctgcc cgacagcgca   2220
ctgtccttgt cgccgcagct gtcgttgccg acgcagtact gctcgacctt gcggtggccg   2280
atgaagcgca ccccggccgg cgaggcctcg tagacgagga attcgcgggc atggccgaag   2340
tgctggttga ccaggccgcc gccgctggtg gccacggcca tcagtaccgg gcgatggccc   2400
ttgtccactg tgccggtgag ctgcgcagcg ctggggtgg ccaggcgcgc cttcttcgcc    2460
gcgcgttcgt ccagctcctc cttgatcgcc gcgtggatgg cggcgcgctt gaccatcgcc   2520
gcctcgtagt cgacgtccat gctctcgatc ttgtcgaggg tgaactcgtc gccgcggtcc   2580
tcgccgagca ggcccaccgc gtcggcgcgg cactggcggc agtggcgcat catgttcatg   2640
tcgccggcac aggcgtcctg caggtcctgc agttcctccg gctccgggct gcgctggccc   2700
atcacgccat agaaggtgcc gtgctcggcc tcggcgatca gcggcatgac gttgtgcagg   2760
aaggcgccct tggccttgac gatgcggctg acctctttca ggtgctcatc gttgacgcca   2820
gggatcagca ccgagttgac cttcaccagg atgccacgct cgaccagcat ctccaggccc   2880
ttctgctgcc gttcgatgag gatcttggcc gccttgcgcc cacggatgcg cttgttgttc   2940
cagtagatcc aggggtagat ctcggcgccg atgtccgggt ccacgcagtt gatggtgatg   3000
```

```
gtcacgtggt cgatgttgtg cttggccagc tcgtcgacgc agtcgggcag ggccaggccg    3060
ttggtggaga cgcacagctt gatgtccggc gcctgctcgg acagcatgcg aaaggtctcg    3120
aaggtgcgct gcgggttggc cagcgggtcg cccgggccgg cgatgccgag cacggtcatc    3180
tgcgggatgg tcgccgccac cgccttgacc ttcttcaccg cttgcaccgg ctccagcagc    3240
tcggacacca cgcccgggcg cgattcgttg gcgcagtcgt acttgcggtt gcagtagtgg    3300
cactggatgt tgcaggccgg cgccaccgcc acatgcat                           3338

<210> SEQ ID NO 6
<211> LENGTH: 39211
<212> TYPE: DNA
<213> ORGANISM: Pseudomonas stutzeri

<400> SEQUENCE: 6
tcagatcttg cgcatatgaa tgttcagcgt ctgcactcgg taggcgatct gccggggcgt      60
catgccgagc aggcgggcgg ccttggcctg acccagccg gcctgttcca gcgcggcgat     120
gacgcgctcg cggtcgtcga ggctgtcgtc ggcgaggtcg acttcgggga ccggcgccag    180
cggcgtggcg tcgtggtcga ggccggtgag ggagaccacg tcgcggctga tggtgccatc    240
ctcgctcatg atggccgagc gttccaggca gttttccagt tcgcgcacgt tgcccggcca    300
gcggtggctc atcagcagac gcagggcgct gtcggtcagc ttgagtttgc gaccctgctg    360
gcgggcgatc ttgtcgagga ggaattcggc cagttccggg atgtcggcgc tgcgctcgcg    420
cagcggcggg acgcggatgg ccatgacgtt gaggcggtag tagaggtctt cgcggaactt    480
gccttgctcc acctcgtgct ccaggtcgcg gttggtggcg cgacgatgc gcacgttgac     540 cttcaccgtc tggctgccgc cgacgcgctc cagctcgcct tcctgcagca cgcgcagcag    600
cttggcctgg aacatcggcg agatctcgcc gatctcgtcg aggaacaggg tgccgccgtc    660
ggcctgttcg aaacgtccct tgcgctgctt cacggcgccg gtgaaggcgc ctttctcgtg    720
accgaacagt tccgattcga gcaggggtttc cggtagcgcg gcgcagttca ggcgtaccag    780
cggctggtga gcgcgcggtg agttgtagtg gatggcgctg gcgatcagct ccttgccggt    840
gccggattcg ccgaggatca gcacggtgct gttccacttg gcgacccgtc gaacctggtc    900
gaaaacccgg cgcatggagg cggtgtggcc caccaccatg ttctcgaagc cgtacttggc    960
gcggacttcg cggcgtagct cgtcgcgctc gtcgaccact tcctggccgt cctcgaggtt   1020
caccaccagg cgcacggtct gcgccagtag gcgggcgacg atttccatca aacgggtgcg   1080
ttcgggcatc agctcgtcgg cgcggcggtc gggctgggca gccagcacgc cgatggtggt   1140
gccgtcgacg gccttgatcg gcacggcgat gaagggcagg tccatgtcgt acagcgccag   1200
tcggtcgaga aagcgcggtt cggcgtcgat acgcccgagc accacgctgt tgccatgctt   1260
gaggatgttg ccgaacacgc cttcgccgat gcggtagcgg gtgctttcgc aggcccgtac   1320
cacggtttcg gagtcgctgt gcacggcgcc cacctgcagg ctgccgtcct tcgggttgca   1380
gatggagacc agcccgtgca gcaggccgag gtcttcgtgc agcacggcga ggatctcggc   1440
cagcagttcc tcgatgggcc ggccgcggtt aaggatgcgg gcgatctgcg ccagcgcctg   1500
cagttgggca tccagcagtt cgttgcgggt tggcgcgctg gggcgttcgg cgaatgtggc   1560
gttcatgcga gcttcccctg tcagctggcc gagaagggca gttcgacgac gatcctgcag   1620
ccctggtcgt agccgctatc gatatgcacc gtgccggcat gctcggtgac ggtttcctgc   1680
accatggcca ggcccatgcc gcgaccgtc ttgtgcgggcg gcttggtgct gaagaagggt    1740
tcgaatacct tgagcgccag ctccggcgcg atgcccgggc cgctgtcggc gatctccagg   1800
```

```
cgcaccaccc gctggccctg gacacgggtg acgatcgaca gcgtgcgcgg gttgtcctgg    1860
ttctggctca tggcctcgat ggcgttttcc agcagctgct tgatcatgct gcgcagccgg    1920
ccttcggcgc ccatcaccca gggtaggcgc agcgccggct gccagtcgac gacgatgccc    1980
tgggcgagca actggtcggt catcaggctg accacttcgc ggatcagctg gttgatgttg    2040
accggcacgc agccgccggc ccggcgctgc ggaatcgagc cgctgaggct tccagcgca    2100 tccatgccag cctggctggc ttcgcgcatg gcgctgagca ccggatcgcc ctcggcgctg    2160
tcgcccaggc gtcgttcgag catgcgcagc gccgcactga tcaggttgac cgggccctgc    2220
aggcggtgga tggcgccgtt gaaggtttcg cgcatgccgt cgagcagctc ttcctcggcc    2280
atcagcacct tcagggcgtt gagctgggag gcctgctgtt gctggcgcag cccggtgatg    2340
tcgttgaccg tcagcagcag gtagttttcc tcgcccgggt cgaagaagtc gtcggcgcgt    2400
tcgccttcga tgaggatggc gcggccatgg caggacagcc agcgcggtgt gtggccgccg    2460
aggtcgaagg tgacttcctt gccggtgaag gcctggccat gcgccttcag cgcctcgatg    2520
gcgccgccga ggttgtcctg cagcaggctc accagttgcg cgggcgtggc ctggtcgccg    2580
agttccgcgg ccaggcggtt gaagctgggg ttggacaggc ggatgcgcag ggcgtgatcg    2640
agcaccacga tggccgccgg tgcgctgtcg accaccgcct cgatgatcag ccgctggttg    2700
ctgacgcgct gttcgagctt gtgctggtcg ctgctgtcgc ggtgcatgcc caggtaatgg    2760
atggtccgct cgtgctcgtc gagcaccggc gccacggtca gctcggcgag gtagcagctg    2820
tcgtccttgc gccggttgac cagcatgccg gaccaggcct ttttctgcgc caggcggctc    2880
cagagcgcct ggtagaccag ccgcggggtg gtgccgttgg acagcaccga ttcgttcttg    2940
ccgatcacct cgctgctgtc gtagccggtg atggcgctga aggcgcggtt ggcatagagg    3000
atgttggcct tcagatcggt gatggaaatg gcgatcggcg cgtgctccac ggcttgctgg    3060
aacacttcgg gcgccaatcc atcggacgca gcgggttgcc ccgcgtcgcg ctcggggtg    3120 gcctgggtca tgtgcatgtc ctcatcgatg cggcgaagcc gacgtctgtg cgccggtatc    3180
cgttgcaaag ccatacggtt aggggctgt tgccgttcgc gagctgcgaa tgaaacggca    3240
acagacccct tagggttttg caaaccgcgt gccgtcggtc acattccttg ccgacagccc    3300
tgcggagccg taaatacgct gtgcagatgg atttctgccc cgacaggtgc cgctgggctg    3360
ttgcaaaacc cacagggagg cgcgcgcact tctcccggcc tgtcgcaaac cccacaaagt    3420
ccgtcgcgcc agcgtcgcca ggggttgcgc tatcacggga ttcgttgatc tgcatcaacg    3480
aatcccgggc tctcggggcg ctccgggacg cccggcgggg cgtggcatgc ttgatgcaaa    3540 accctcaca caaggcctt tgcccgacaa cggtgcaagc gctgccaata ggctgggagg    3600
ggttatggaa tatgcgctgt ttctgatcgg caccgtgctg gtcaacaacg tggtgctggt    3660
ctacttcctc ggcctgtgtc cgttcatggg ggtctccggc aagctcgacc cctcgctggg    3720
catgggcttg gcgacgaccc tggtgatgac cctgggcggc gtcagcagct ggctgctaga    3780
acgctacgtg ctgcagccgc tgggcatcgg cttttttgcgc atcctctcct acatcctggt    3840
gatcgccggc ctggtgcagc tgatcgagat gatcatccgc agggttagcc cgccgctgta    3900
tcgctcgctg ggcatctacc tgccgctgat caccaccaac tgcgccgtgc tgggcgtgcc    3960
gctgatcagc gtgcgcgaag gccacaggct ggccgaggcg gggctgttcg gcctgggctc    4020
ggcgctgggc ttcaccctgg tcatggtgat cttcgccggc ttgcgcgagc gcctggcgct    4080
ggccagcgtg ccggcggcct tcgccggcgc accgatcgct ttcgtcaccg ccggggttgct    4140
```

```
ggcgatggct ttcatgggct cgccggcct gatctgaaac gcacgccgcc ggcgaggctg    4200
gcgaaggagg agcaatgctg gacgcaattc tggttcttgc actgatgggc ctgctgctcg    4260
gcggcggcct cggtctggcg gcgcgctatc tggcggtttc gcaggagaac ccgctgatca    4320
aggaaatcga ggcgctgctg cccggcagcc agtgcgggca atgcggctat ccgggttgca    4380
gtgcggcggc cgacgccttg gtcgagggca gcgccgcggt cacctgctgc ccgcccggcg    4440
gggccgcgct ggccgagcgc ctggccgaac tgctcggcgt gccgctggac gccagtgcgc    4500
tcgccgcgcc catgctggcg cgcatcgacg ccgccgagtg caccggctgc acgcgttgct    4560
tccgcgcctg cccgaccgac gccatcgtcg gcgccaacgg gcagatccat gcgtgttga    4620 gcaatgcctg cattggctgc agcaaatgcc tggaggcctg cccggaggac tgcatcgccc    4680
tcgcgcccca gacactgacg ctggaccact ggcgctgggc caaacccagg gccgcctgat    4740
ttcgcctgat gaacaggggc gtcagacccc gggagtcgaa atgttcaac ctcgcgcatt    4800 ttcgcggcgg catccatccc gccgcccaca aggaccgctc ggccgccctc ggcatcgccg    4860
tgcagccgct gccgccgcgc ctgtacctgc cgtttcgcca gcatgccggg gccgaggcct    4920
tgccgctggt gaaggcgggc gagcgggtgc tcaagggcca gctgctggcc ggctcgccca    4980
ctgagctctc ggcgccgatc catgcgccga gttccgggcg catcctctcg atcgggccga    5040
tcgacgcgcc gcatccgtcg gggctgcagg tcaacggtgt ggtcctcgaa tgcgatggcg    5100
aggagcgctg gatcgagcta gacgtaccgg ccgacccctt cgccgaggac ccgcagcggc    5160
tcgcccagcg cgtcgccgat gccggcgtgg tcgggctcgg cggggcgatc ttcccggccg    5220
cggtgaagct caagcagggc gcccggcacg agatcaagac cgtgctggtc aacggcagcg    5280
agtgcgagcc gtacctgagc tgcgacgacc ggctgatgcg cgagcgcgcc gaggcggtgg    5340
tcgatggcgc gcggctgatc cagcacatcc tgcgtgccta cagcatcgtc atcgccatcg    5400
aggacaacaa gccggcggcg ctggcggcca tgcgtgctgc gagcgagccc tacggcgcca    5460
tcgaggtggt ggcggtgccg gcgctctacc cgatgggctc ggccaagcag ctgatccgcc    5520
aggtcaccgg ccgcgaggtg ccggccggcg ggcgcagtac cgacgtcggc gtgctggtac    5580
acaacgccgg cacggtgtat gcgatccagc aggcgctgcg ccacgccgc ccgttgatct    5640 cgcgggtggt gacggtggct ggtggttgcg tgagcaaccc gcgcaacatc gagactctga    5700
tcggcacccc ggtgcaggcg ctgttcgaaa gctgcggcgg actgctgcgc gagccgcagc    5760
aactgctgct cggcgggccg atgatgggca tgctgctgcc atccacggcg gtgccggtga    5820
tcaagggcgc caccgggctg ctggcgctcg accacggcga agtgccgcgc agcgacagcg    5880
cgccgtgcat ccgctgcgcg cgctgcgtcg acgcctgtcc gatgggcctg ctccgctgg    5940 agatggccgc gcgcacccgc gtcgacgatt tcgacggcgc cagcgaatac ggcctgcgcg    6000
actgcatcct ctgtggctgc tgcgcctatg tctgcccctc gcacattccc ttggtgcagt    6060
acttccagta cgccgtcggc cagcaggacg agcgccgcag cgccgcgcgc aagaacgatt    6120
acgtcaagca gcttgccgag gcacggcgg cgcgcttggc cgaggaggaa gcggccaagg    6180
cggcggccaa gcggcgaag aaacgcaagg cggcggcgcc ggccgccagc gaggtatcgc    6240
catgagcgcg cagggtatcg cggcggggcc gttcgcccat gatcgctcct cggtcgaccg    6300
catcatgctg cacgtctgcc tggcgttgct gccgacgacg gcctggggcc tgtatctgtt    6360
cggctggccg gcgatctacc tgtggctgct gacctgcgcc agcgcggtgg cctgcgaggc    6420
cgcctgcctg tacctgctcg gccggccgct gcgccgcctg ctggacggca gcgcactgct    6480
cagcggctgg ctgttggcac tgacgctgcc gccctgggcg ccctggtgga tcgccgtcgg    6540
```

-continued

```
tggcagcatg ttcgccatcg gcattggcaa gcagctgtac ggcggcgtcg ggcagaacgt    6600
gttcaacccg gcgatgctgg cgcgggtggc gctgctgatc gccttcccgc tgcagatgac    6660
cacctgggcc ctgcctttgc cgctgggtac ggagggcgcg cccggctggc tcgaaggcct    6720
gcgcatcacc ttcgccggtg gggcgctggc cgatggcctg agcggcgcca ccgcgctggg    6780
ccacctgcag accgagctga ccctggggca cagtgccgcg cagatcctcg acgggcattt    6840
cgcgttgctg ccggccttc tcggctacag cggcggcagc ctcggcgaga cctcggagct     6900
gctgatcctg ctcggcgggc tctggctgct ggcactgcgc atcatccact gggagatccc    6960
gctgggcatg ctgctgacgg tgggcgcgct ggcggcgctg gcgaaccaga tcgacccgca    7020
ggtacatggc ggcgggctgt tccacctgac ctcgggcggc ttgctgctcg gcgcgttgtt    7080
catcgccacc gatccggtga cctcgccgat cagccgcagt ggccggctga tcttcgccat    7140
cggttgcggc gcgctggtct tcgtcattcg cagctgggc aatttccccg aagccgtggc     7200
gttcgccgtg ttgctcatga acgccctggt gccgctgatc gaccgcgtct gccggccgcg    7260
tgcctatggc cgcaacgcgc gcggcaagcc gctggtggcg gcgaagtgga cccgccaggt    7320
gaaggaggtc gacaaggtat gaacgagctg acccagacgc cgcccgtggc agacggcaac    7380
gaaccgccgc tcacccgacc cggcctggtc gagacctggc gcgagcgggt ttcctaccag    7440
gcgctgtcgc tgggcttggt ctgcgccctg gtggccgtgg cgctgctgct cggcaaccag    7500
ctgacccacc agcggattgt cgacgccgag cggcaggacc gcctcgccgt gctgcgccag    7560
gtgctgccgc aggcgctcta cgacaacgat ccgctggccg atgccttcaa cgtcgaggat    7620
gccgagctgg gcctgatcga ggtgtacccg gcgcggcgcg cggggcaact gacggccacc    7680
gccttccaga tcagcaccgt cggctacggc ggcccgatcg tccagttcat cgccctcgac    7740
agcgaaggcc gcatcctcgg cgtgcgggtg ctcagccaca aggaaacccc tggcctggcg    7800
gacaagatcg aagtcacccg cagcgactgg atcaaggcct tcgacggcct gtcgctggcc    7860
agcacaccgc tggatcagtg ggcggtgaag aaggacggtg gccagttcga ccagttcgcc    7920
ggcgccacca tcaccccgcg ggccatcgtc aagggcgtgc tccgggcgct cgagttccag    7980
gcccgccagt ccaccgccca gtccaaccag gagactcggc catgagcagc caatgcggat    8040
cagcggatgt cacggcgccc aagcccaagg ggctgttcaa ctacttcagc tcggcgctgt    8100
gggactacaa cgtcgccctg gtgcagatgc tcgcgttgtg cccggcgctg gcggtgacca    8160
ccaccgctac caacggcctg gcatgggcc tggccaccac cctggtgctg atgatcacca     8220
atgcgatcat ttccgcgctg cgccacagca tttcgccggc ggtgcgcaac ccgctgatga    8280
tcggcatcat cgccggcgtg gtgaccctca tcgacatggc gatcaatgcc tggatgcacg    8340
aactgtacaa ggtgctgggg ctgttcatcg ccttgatcgt gaccaactgc gcggtactcg    8400
gccgtgccga atcgttctgc agccgcaacc cggtgctgcc ctcgatcctc gacggcgccg    8460
gcatgggcat cggcttcacc tgggtactgg tggtgatcgg cggatacgc gagatcctcg     8520 gcagcggcac gttgttcgcc caggcctcgc tgctgctcgg tgagcacttc cgctggctgg    8580
agatcaccgt cctgccccgg cttccagggca tcctgctggc gatcctgccg cccggggcgt    8640
tcattgttct gggcttcgtg ctggcgttca agcgagtagt tgatcgccgg cgcgccgagc    8700
gacggatcag gacccatggc gaactggtag tgttgcagtg agcccggccg aggagcgaag    8760
cagacgatga agatttccgt tgtatacgcc gcacccgc agccctgct gttcgattgc       8820 cgggtggcgg aaggctccag cgtggccgag gccatcgagc actccggggt gctgcgctac    8880
```

```
tgcccggaca tcgacctgag caagcaaaag gtcggggtct acggcaagtt cgtcaaactc    8940
gacagcccgc tgaaggaggg cgatcgggtg gaaatctacc aacgcatcac gcgcgtgctg    9000
gatgaagacg acgatgacga cgactgacag ccgccgcgga tgaccatagc cgagagagga    9060
gcgaccgatg aacagccagc ccccgagcat gaaccgtgaa accgcattac gcatcgcact    9120
ggccgcccgg gcattgcccg aggtgggcgt cggccggttg ctggatatcc tgcaccagcg    9180
gatcgatgga gaactgaacg aagagagcct gcagcgcgtg accgtcaccg acctcaagac    9240
ggcgttcgcc agcgccgacg gcgaggagga tggcgaggac atcggcatcg gcctgccggc    9300
gctgaaggaa gcggtgcgca tcctctgggg cgaaggcgtc ggcgacgacc tgccgcagcc    9360
ggaggtcctg gaccgcgtgc cggaaggctc gatccgggtg gccatcgcct ccaacaacgg    9420
cgagcgcctg gacggccatt tcggctcgtg cctgcgtttt ctgatctacc agatcggcct    9480
cgacagcctg gcgctggtgg acgtgcgctc ggcgctggag accgagttcg ccgaggatcg    9540
caatggcgcg cgtgccgagc tgatcggcga ctgccaggtg ctctatgtgg tctccatcgg    9600
cggtccggcg gcggccaagg tggtcaagac cggcctgtac ccgatcaaga aggccggtgg    9660
cgaggcccgg cagattctcg ccgacctgca gaccgtcatg gccggcaacc cgccgccgtg    9720
gctggccaag ctgctgggcg tgagcgccga gcagcgagtg cgcttcgacc gctccgacga    9780
cgaggcggcc tgggcatgag cgatgtgcgc aggctggtcg ccgtggccat cgaccgccag    9840
ggcaaggtcg ccggtcacgc cggtcgggcg caccactggc aggtgtacga catctggccc    9900
ggcgaggcgc cggaatccgt ctatcgcctg gcgctggacg aacaggcctg cctgcacgag    9960
tggcatgtca gcgcgcaacc ggaacgccat ccgctgcacg cggtggacgt ggcgatcgcc   10020
gccagcgccg gcgacggcgt ggtgcgtcgc ctgggcgagc gcggcgtgac gctgttgacc   10080
accgccgaga gcgacccgga acatgccgtt aaagcctggc tcgccggcag cctgccgcca   10140
ggcttgccgc acgaggagcc gggctgcggc ggcgagggc accggcatcc ctgagcgtgc   10200
ggggatggga cggatggcaa ccccaggctg ggtcgagccg cgcagcggcg aagcccaacg   10260
tcgtgcgggc tcaagcccgt gcaaccggca ttgttcgtga aacaccatgg ggcggatgtg   10320
gcgcctgatg atccgcgatg ttgggcttcg cttcgctcaa cccaacctac ggcaccgggg   10380
cgataggcaa aaaaactccc ctgggagcgc aggggagtgg ctcatcgcca atatggggat   10440
gtcaaaccgt tgcacgtgac ccgggctgcg cccgggctct gcgagcccag ggcaacctag   10500
ggtggaatcg agcccccatgc tggccaagcc caatacgccc ctgggtggtt cagatcggcc   10560
cgcgcgcctc gcgacgatgg gcgacggtgc agccaagggc ggcctcgtag ctcagcgtct   10620
ccagcttcgg ccggtagtcg cgcagcgcgg cgtagacggt gagtaccttg tcctcggcgc   10680
tctggccctt gaagtcttcc ttgtccaggc gcaggtcgtc ggccagggtg ttccacaccg   10740
cgccttcctc gtgcgcctgc agctgcaggg tcatgccgtc gagctcggtg tacagcgact   10800
ggccgaggtt ctccacgtag aagatcaccg gtgcgccgtc ggccaggtcg cggcgatagc   10860
gttcgaggaa cagcggcagg tgggccagtt cgatcagggc gccggccatc atcgccagtt   10920
tccccctgctg ctcgagcatg accgcctgct tgaccacggc ggtcggcggc aggcggcggc   10980
cggaggcgtc ggcgatctcg ccttcttcga gcaccaggtc gccgcggaag gcgtaggtgt   11040
ccggcgtcgt ggtcgcgcca ttgacgctga cgttgcacag caggttttgc gtttcgtagg   11100
ttttcaacag catggtcatg gtctctcgtg gaaaaaatgg tcaggcgact tgtggggcgc   11160
cctgggtcag gccaagcagg tcgtgccaat cggtctcgac cagttccagt tgcttgcgca   11220
ggcagaccct gcggtccttt gcgctgggcg aggggatcag cgcccagccg gcgggcgcgg   11280
```

```
ctgcatcgtg gatcaggtcg ctcatcagca tgcgctcggt gtcgcggttg aactgcatgc    11340
cgaggaacag gtagcggcat tccttgcgct gcagcttgag ccagccggga atggcgaaac    11400
cgcccatcag ttcggtgatg tagtcgacga agtcggcgtc gctggcgacg taggaagggc    11460
tcggcagcgg cgtgcccagc ggcttgaaca gcaccggtag cgcgggattg acctcgctct    11520
ggtcgatgcg ctggtagcgg cctgcgtcga agcgatagat gtcgaagcgg tagggctgg    11580 cggcgatgcg cgcggcgccg accaccaggg tatgcggacg gtcggcatag cagcgctgca    11640
gctgggtgtc gcgattgcaa tcgatgacgt agggcaggtt cagcccggcc agccagcggt    11700
gcagcggcgc gggcgtccag ttgtcgccgc cgtaggtctg agtcaggaag cgctcgatga    11760
agctgcggcc cttcttgttc tccaggtgca tggcggcacg cgggaattcg tacatcagcc    11820
gcggcgccat cggctgcccg ccgttcatgg cgaggatcag gctttcattg tcggccggca    11880
tcggctgacc tgtgtcgcgg tcgaccacgc cgcccagcac accggggccc agatagggca    11940
ccagttcatg ggcggcgagg cggtcggcga tttcctgcaa aggatcgttc acggcaaatc    12000
tcctgcggcc agtggattta ccgatagccg atcgcaataa ccgagccagc cgggagcgtg    12060
catgcaaccc cttgatatat ggggctttga atgcggcgat agttgccgtt caggtgtttt    12120
cgaaagtatc gaacgcgaca attgtcatgt tcgcaacagt tgccgaaagt gtggaaaacc    12180
ggcgcttggc ccgccgatc tttttgtcgc cattgcaaca gtcaggcctg tcggttgtta    12240
actatcgaac cgccgaagga tgttgctagt aattaaatta ttctaattaa acaagtgct    12300 tagattattt tagaaacgct ggcacaaagg ctgctattgc cctgttgcgc aggcttgttc    12360
gtgcctatag cccacgtcaa gtggtaacga aacctgagga acttaattat ggcaatgcgt    12420
caatgcgcta tttacgggaa gggtggaatc ggcaaatcca ccacgaccca gaacctcgtg    12480
gcggccctgg ccgaactcgg caagaaggtc atgatcgtcg gctgcgaccc caaggccgac    12540
tccactcgcc tgatcctgca ctccaaggcg cagaacacca tcatgaaat ggccgccgag    12600 gccggtaccg tggaagacct ggaactcgag gacgtgctca agaccggcta cggcgacatc    12660
aagtgcgtcg agtcgggcgg tccggagccg ggcgtgggct gcgccggtcg cggcgtgatc    12720
accgcgatca acttcctcga agaggaaggc gcctacgagg atgacctgga cttcgtcttc    12780
tacgacgtgc tcggcgacgt ggtctgtggc ggcttcgcca tgcccatccg cgagaacaag    12840
gcccaggaga tctacgtggt ctgctccggc gagatgatgg cgatgtatgc cgccaacaac    12900
atctgcaagg gcatcgtgaa gtacgccaac tccggcagcg tgcggctcgg cgggctgatc    12960
tgcaacagcc gcaacaccga ccgcgaggac gagctgatca tggccctggc cgacaagctg    13020
ggctcgcaga tgatccactt cgtcccgcgc gacaacgtcg tgcagcgcgc cgaaatccgc    13080
cgcatgaccg tcatcgagta cgaccccgcc gccaagcagg ccgacgaata ccggaccctg    13140
gcgaagaaga tcgtcgagaa caagaaactg gtcatcccca ccccgatcag catggacgag    13200
ctggaagcct tgcttatgga gttcgggatc atggacgagg aagacatgac catcgtcggc    13260
aagaccgccg ccgaggaagt cgttgcctga tcgcttcagc agaacggggc agggcggatg    13320
ggccctgccg gggtgtcgca ccgtgcctgg cacggtgcgg tgcgcccgtg acccgcacat    13380
gaacgcaaga ggaggtcaat catgaccggt atgtcccgcg aagaggtgga atccctcatc    13440
caggaagtcc tggaagtcta tccggagaag gcccgcaagg accgcgccaa gcacttgtcg    13500
cccaacgacc cggcgcttga gcaatcgaag aaatgcatca cttccaacaa gaaatcccag    13560
ccgggtctga tgaccatccg gggctgcgcc tacgccggct cgaagggtgt ggtctggggg    13620
```

```
ccgatcaagg acatgatcca catttcccac gggccggtgg gctgtggcca gtactcgcgc   13680
gccgggcggc gcaactacta catcggtacc accggggtga acgcctttgt gaccatgaac   13740
ttcacctcgg atttccagga aaggacatc gtcttcggcg gcgacaagaa gctggccaag    13800
ctgatcgacg agatcgagac gctgttcccg ctgaacaagg gcatctccgt gcagtccgaa   13860
tgccccatcg gcctgatcgg cgacgacatt gaggcggtcg ccaagaagaa ggccgccgag   13920
cacgaaacca ccgtggtacc ggtgcgctgc gaaggtttcc gcggggtgtc gcagtccctc   13980
ggccaccaca tagccaacga cgccatccgc gactgggtgc tggacaagcg cgacgatgac   14040
accagcttcg agaccacgcc ctacgacgtt tccatcatcg gtgactacaa catcggcggc   14100
gatgcctggt cctcgcgcat cctgctcgag gaaatgggcc tgcgcgtggt cgcgcagtgg   14160
tccggcgacg gcacgatttc cgagatggaa ctgacgccca aggtcaagct caacctggtg   14220
cactgctacc gctcgatgaa ctacatctcg cggcacatgg aagagaagta cggcattccg   14280
tggatggagt acaacttctt cggcccaacc aagaccgccg agtcgctgcg ggccatcgcc   14340
gagcatttcg acgacagcat caaggccaag tgcgagcaag tgatcgccaa gtaccagtcg   14400
gagtgggagg cggtgatcgc caagtatcgc ccgcgcctgg aaggcaagcg cgtgatgctc   14460
tacgtcggcg gcctgcgtcc gcgccacgtg atcggcgcct acgaggacct gggcatggaa   14520
gtggtcggca ccggctacga gttcggccac aacgacgact acgaccgcac cctcaaggaa   14580
atgggcaacg ccacgctgct ctacgacgac gtcaccggct acgagttcga ggagttcgtc   14640
aagcgcatca gcccgacct gatcggctcc ggcatcaagg aaaaatacat cttccagaag    14700
atgggcattc cgttccgcca gatgcactcc tgggattatt ccggcccgta ccacggcttt   14760
gacggcttcg ccatcttcgc ccgtgacatg gacatgaccc tgaacaaccc gtgctggaag   14820
aagctgcagg cgccctggca gaaggccgag gaatcggccg agaaggtcgc cgccagcgcc   14880
tgatggtccg cagtcgtacg caacgtccgc ggcggccggc gcaggccggt cgctgccgac   14940
atccgtgatc gccgttcaca gatgagtgag gcgaaggaga gagtcatgag ccagcaagtc   15000
gataacatca aacccagcta tccgctgttc gcgcgacgaag actacaagga catgcttgcc   15060
aagaagcgcg atgccttcga ggagaagcat ccgcaggaca gatcgacga agtcttccag    15120 tggaccacca cccaggaata ccaggagctc aacttccagc gcgaagccct gaccgtgaac   15180
ccggccaagg cctgccagcc gctgggctcg gtgctctgcg ccctgggctt tgagaagacc   15240
atgccctacg tgcatggctc gcagggttgc gtcgcctact tccgtaccta cttcaaccgg   15300
catttcaagg aacccatctc ctgcgtgtcg gactccatga ctgaagatgc ggcggtgttc   15360
ggcggccagc agaacatgaa ggacggcctg gccaactgca aggccaccta caagccggac   15420
atgatcgccg tgtccaccac ctgcatggcc gaggtcatcg gcgacgacct caacgccttc   15480
atcaacaact cgaagaagga gggcttcatc cccgaggact acccggtccc ctatgcccac   15540
accccgagct tcgtcggcag ccacgtcacc ggctgggaca acatgttcga gggcatcgcc   15600
cgctacttca ccctcaatca catggacgac aaggtggtcg gtagcaacca caagatcaac   15660
gtcgttcccg gcttcgagac ctacctgggc aacttccgcg tgatcaagcg catgctcaag   15720
gaaatggacg tcggctacag cctgctctcc gacccggaag aagtgctcga taccccggcc   15780
gacggccagt tccgcatgta ctccggcggc accacccagg acgagatcaa ggatgcgccc   15840
aacgccctga cacccctgct gctgcaaccc tggcagttgg aaaagaccaa gaagttcgtc   15900
gaaggcacct ggaagcacga gacgcccaag ctgagcatcc ccatgggcct ggactggacc   15960
gacgagttcc tgatgaaggt cagcgagatc accggccagc cgatccctga aagcctggcc   16020
```

```
aaggagcgcg gccgcctggt cgacatgatg accgactcgc acacctggct gcacggcaag   16080
cgcttcgcgc tctggggcga tccggacttc gtcatgggca tggccaagtt cctcctggag   16140
ctgggcgccg agccggtgca catcctcgcc cacaacggca acaagcgctg gaagaaggcc   16200
atggacgcga tcctggagtc ctcgccctac ggcaagaact gcaccgtgta catcggcaag   16260
gatctctggc acatgcgctc gctggtgttc accgacaagc cggacttcat gatcggcaat   16320
agctacggca agttcatcca gcgcgacacg ctgcacaagg gcaaggaatt cgaggtgccg   16380
ctgatccgtc tcggcttccc gatcttcgac cgccaccacc tgcatcgcca gaccaccctg   16440
ggctacgaag gcgccatgca gatgctgacc accctcgtca atgccgtgct cgagcgcctc   16500
gacgacgaga cccgcggcat gcagagcacc gactacaact acgacctggt tcgttgaccg   16560
ctagcgggga gggcgacctc cccatcctgg ccggccgacg caccgcaatg gtcgtcggcc   16620
ggccagccct atttcagga agcctcccat gcccagtgtc atgatcagcc gtaacaagaa   16680
tggccagctg accttctaca tcgccaagaa ggaccaggaa gaaatcgtcg tcagcctgga   16740
acacgacagc cccgagcgct ggggcggcga agtcgccctg gccgatggct ccagctacta   16800
cctcgaaccc ctctcggcac cgccgaaact gccgatcacc ctgcgcgcca aacgggccgg   16860
cgagggctga acgatggcgc ccagcaacgg acgggctccg ctgccggctc acctggccct   16920
gcgcatcgcc ctggcggcgc gcgagctgaa cggcgtggat accgggcaac tgctgcgcac   16980
cctgctcagc gtcaccggcg agccgatcac cgaagcgcgg ctggccaggc tgcgcctaaa   17040
ccgcctgcgc aaccgcctgc tgagcagcgt cgacgggcca ccgccggtgc tcagcgagcg   17100
gcaattgcag cgtgcgctcg gcctgctcaa ggggcgtggc gtgcgaatgc ccgaggaacc   17160
gttgccggcc atcgagccct atcgcgaagg cgagttgccg gattcgatcc gcatcgcctg   17220
cacctccgac ggcggcgagc gcctggacgg cagcttcggc agctgcgcgc gctttctcgt   17280
ctaccagatc tcgccgagcg ccagccgcct gatcgacctg cgcgagccgg ggccggccgc   17340
gccccacgag gatcgccatg cccgccgcgc cgaactgctg cacgactgcc agctgctcta   17400 cacccctgagc atcggcgggc cggcggcggc caaggtgatt cgcgtcggca cccacccggt   17460
caaggtcatg cggccgatcc cggccgcgca gatcgtcgag gaactgcaac aggtactggc   17520
cagtgcgccg ccgccctggc tggccaaggc tatgggcagc gagccggcac ccgcgtttc   17580 catgtctgaa aaagaggaca ccccatgatc agtcagaccc agctcgacgc ggtcatccgc   17640
caggccgaga acggcccgct gaacgaggcg ctgctcgcca ggctgcgcag cgagcaccct   17700
ggtatccact tcacctgttg catggacgac gacgtggtgg tcaacgccaa gccggttgcc   17760
gagcggccgg ggttcaacgt ctatctggtc aactccagcc agcactgctc ggtgctgagc   17820
aacgacctgg acgccgcctc gggcatcgtc ctggccgaag tcatcgccga ttagagagcg   17880
cccatgcaga acgacggtag cgaggacatt atccccctgg cggactgccg cgattgcagc   17940
tttcgcggcg acctgctgcc cagcggccgc tgcacgccgg cgaccgctg cgtagcgatc   18000 cacagcggcc ggcagatcga ccgtttcttc cggcagaatc cgcagctggc cgtacactac   18060
ctggccgatc cgttctggga gcggcgcgcc atcgccgtgc gctacgcccc ggtggaggcg   18120
ctgctgtcga tgatccacga cgtcgacgag gcggtgcgtc gtgccgtcgc ctaccgcctg   18180
ccgcgcgagc gcctgggcga actcatgcgc gacccggatc gggaagtacg catcaccgtc   18240
gccgaccgcc tgccggccga gcagctggaa cggatggctg ccgacccgga ttacctagtg   18300
cgcgcctacg tggtccagcg catcgcccca gggcggctgt tccgcttcat ccgcgacgag   18360
```

```
gaccgccagg tgcgcaagtt cgtcgcccag cgtctgcctg aggaaagcct cggactgatg   18420
gtcaccgacc ccgaaccgga agtccgccgc ctggttgccg cgcgcctgca tggccaggac   18480
gtgctggaaa tgctccacga ccccgactgg acggtacgcc tggccgccgt ggaaaacgcc   18540
ccgctcgagg ccctgcgcga gctgaacgaa gacgatcccg aagtccaggc tgcgatcgcg   18600
caacggttgg ggtaggttgg gtggacgccc gacccgagat gatgcttttt aggctttggt   18660
aggcctgccg gcctgcatcg ccgcgagggc gcgcctccca caggtccgca ggctgcttgc   18720
tgcctttgtg agcccgacca cggggcgatg cttttcgcta gggtgggccg ggcggcgttc   18780
cgcttcagcc caccaatcaa gccagcgatc gcgaaggatg ctggtgggct gatgcccacc   18840
ctacggatcc gtaccgcccg acccggccta cggggccact cgccgaatcc tttgttgcga   18900
acccgacatc tgggcgcgtt tgcgacaatt ttatttcaat gaaaatcata taaatcaatg   18960
agttaatttt tggtacaggc attgcactca cctcgttgcg cataaccacg acgaccggag   19020
ggtgcgatga agccaagga cattgccgag ctgctcgacg agcccgcctg cacgcacaac   19080
aagaaggaga agtccggctg cgccaagccg gcgccgggcg ccaccgatgg cggctgcgcc   19140
ttcgacggcg cgcagatcgc gctgctgccg atcgccgatg tggcgcacat cgtccatggg   19200
cccatcgcct gcgccggcag ttcctgggac aaccgcggca cccgctccag cggcccgcag   19260
ttgtaccgca tcggcatgac caccgatctc tccgagcagg acgtgatcat ggggcgcgcc   19320
gagaagcgcc tgttccacgc catccgccag gcggtggaga gctacgcgcc gccggcggtg   19380
ttcgtctaca cacctgcgt gccggcgctg atcggcgacg acctcgacgc cgtgtgcaag   19440
gccgccagcg agcatttcgc caccccggtg gtgccggtgg acggcgccgg tttctacggt   19500
accaagaacc tcggcaaccg catcgccggc gatgccatgg tcaagcacgt gatcggcacc   19560
cgcgagcccg acccgctgcc ggccggcgcc gagcgcgccg gtattcgcgt gcacgacgtc   19620
aacctgatcg gtgaatacaa catcgccggc gagttctggc acgtgctgcc gctgctcgac   19680
gagctgggcc tgcgcgtgct ctgcacgctg tcgggcgatg cgcgttttcg cgaggtgcag   19740
accatgcacc gcgccgaggt gaacatgatg gtctgctcca aggccatgct caatgtcgcg   19800
cgcaagctgc aggagcgctt cggcacgccc tggttcgagg gcagcttcta cggcatcacc   19860
gacacctcgc aggcgctgcg cgacttcgcc cggctgatcg gcgacgacga cctcgccgcg   19920
cgcaccgaag cgctgatcgc gcgcgaggaa gcgaggattc gcgcggcgct ggagccctgg   19980
cgcgaacgcc tggccggcaa gcgcgtgctg ctctacaccg gcggggtcaa gtcctggtcg   20040
gtgatctccg cgctgcagga cctgggcatg aaggtggtcg ccaccggcac caagaaatcc   20100
accgaggagg acaaggcgcg catccgcgag ctgatgggcg acgacgtcaa gatgctcgac   20160
gagggcaacc cgcgcgcgtt gttgcgcacg gtggaggaat accgcgccga catcctcatc   20220
gccggcggtc gcaacatgta caccgcgctc aaggggcgca tccccttcct cgacatcaac   20280
caggaacgcg aattcggcta tgccggctac gacggcatgc gggaactggt gcgccagctg   20340
tgcctgaccc tcgagagccc ggtgtggccg gcggtgcgcc agccggcgcc gtgggagcgg   20400
cccgcgtcgg ccgaggcaca accccgcacg ctggcgaacg cctgaggagg tcgcgatggc   20460
acagatcatc aaccgcaaca aggcgctggc ggtcagcccg ctgaaggcca gcagaccat   20520 gggtgccgcg ctggccttcc tcggcctggc gcgcagcatg ccgttgctgc acggttcgca   20580
gggctgcacg gcgttcgcca aggtgttctt cgtccggcac ttccgcgagc cggtgccgtt   20640
gcagaccacg gcgatggatc aggtcagctc ggtgatgggc gccgacgaga acgtggtcga   20700
ggcgctgcgc accatttgcg acaagcagca tccagcggtg atcggcctgc tcagcaccgc   20760
```

```
gctggcggag acccagggct gcgacctgca cagcgccgtg catcagttcc gccgcgaata   20820
tcccgagtac ggcgacgtgg ccgtggtgtc ggtgaacagc ccggacttca gcggttgctt   20880
cgagagcggt ttcgccgccg cgctcaaggc gatgatcgag gcgctggtgc ccgagcgccg   20940
tgaccaggtc ggccagcggc cgcgccaggt caacgtgctg tgcagcgcca gcctgacacc   21000
cggcgacctg gaattcgtcg ccgagagcat cgagagcttc ggcctgcggc cgttgctgat   21060
ccccgacctg tccggctcgc tggacggcca tctcgacgag gcggccttca acccgctgac   21120
caccggcggg ctgaccctcg acgagttggc cagtgccggg cagagcgccg ccaccctggt   21180
gatcggccag agcctgaccg ccgccgccga tgcgctggcc ccccgcagcg gcgtaccgga   21240
ccggcgtttc ggcctgctgc tgggcctgga ggcggtggat gcctggttga tggcgctgag   21300
cgagatcagc ggcaacccgg tgccggagcg ctggcagcgc cagcgccggc aactgcagga   21360
cgccatgctc gatacccatt tcatgctcgg cgacgcgcgt ctgggcatcg ccgccgaccc   21420
cgacctgctg ctcggtttct ccaccctggc gcgcggcatg ggcgcgcaac tggtggccgc   21480
cgtggtgccg gcgcgcgcgc cggcgctggc cgatgcgccg ctggcgcgca tccaggtcgg   21540
tgacctggag gacctggagc aggccgcccg cgacggtggt gcccaactgc tgctcggcaa   21600
cagccacgcg ctggccagcg ccgaccgcct gggcattccg ctgctgcgcg tgggctttcc   21660
gcagtacgac ctgctgggcg gcttccagcg ctgctggagc ggttaccggg ccagcgcgca   21720
ggcgctgttc gacctggcca acctgctcac cgaacaccat cagggtatcg cgccgtatcg   21780
ctcgatctat gcgcagaagc ccgcctccga ccattcgcaa tggagccact gagccatggc   21840
cagccccatc cgacaactgc aggtactcga cggcgagaac gacggcacgc tgctcaaggt   21900
ggccttcgcc tcgtccgatc ggcgcacggt cgaccagcat ttcggttcgt cgcggtcgtt   21960
cgtgttctac ggcatcgacc ccgagcgggc cgagctgcaa tcggtggtgg aattcggcga   22020
gctcgaccag gacggcaacg aggacaagct ggcggccaag ctggaactgc tcgatggctg   22080
catcgcggtg tactgccgcg cctgcggcgc ctcggcggta cgccagctgc tggcgatcgg   22140
cgtgcagccg gtcaaggtca gcgaggccga gggcatcgcc gaactgatcg aaacgctgca   22200
ggccgagctg cgcgaaggcc cttcggcctg gctggccaag gcgatccggc gtaccgtgg   22260
cacgccggac cagcaacgtt tcgaggccat ggccggcgag gcctgggacg aatagcccga   22320
cacccgcaat cgaggacagc gttatgtatg cagaagaaca acaggcggtc gttcgcgacg   22380
acgccccggc cctgcaggac ccggtgatca agcagatggt ggtgcaactg cgcgccatgg   22440
acagctacgg cacctacgac acctggagcg acgcgcgggt gctcgacccg ctggtgctga   22500
cccgcgagcg gcgccgcgcg atccccatcg tcggcgatcc ggacgaggtc accctgtcgc   22560
gggtcaaggc cttctacaac gccctggcgc agatgatcga gcgcgagacc gggctgctcg   22620
cggtaccggt gatcaacatc acccacgagg gcttcggccg cgcgctgatc ctggtcggca   22680
agctggtggc gctggacaag accctgcgcg acgtccatcg cttcggcttc gaatcgctcg   22740
aggcgttgtc gctcgacgcg cagaagctgc tgggcaaggc gaccgcgctg gtcgccgagc   22800
accgtacggt cgccgagttg taaggggaga cgagccgatg accgaagagg aactcaaggc   22860
gttgaagaag gaagtcagcc agaagaagcg catcgccacc gaatgggcgt cgcagatcca   22920
cgacctggtc gaggaccggc tgctgatcga ttaccggcaa ttgccggaac tggcgacgca   22980
ggcacaccag gcctgcctcg actgggccga ggccaacgcc cggctggaag cggcggcaa   23040
cgcctgaccg ccaatacaga gcgggcccga gcccgccgta tccctaaccg taggccgccg   23100
```

```
ccatgccatt ggcgggcagg agatgacaga tggaagcagt gataaccggg cgtacgcgcg   23160
gtggcgccga atgggtgccg cagttcgtca ccgccgtcga tgcgcagaag tgcatcggtt   23220
gcgggcgttg ctacaaggtg tgcccgcgcg acgtgttcga gctggtggag cgctccggca   23280
tggtgggcga ggacgacgac ctctacgacg aggacgacga gatgatggtc atggccatcg   23340
ccgacggcct cgactgcatc ggctgcaagg cctgttcggc ggtctgcccg aaacaatgcc   23400
atacccatca ggccctggcc ggctgaggag ctgctgacat gccaagaccc gactaccaca   23460
tcttcctctg cctgcagcgc cgcgccgagg ggcacccgcg cggcagttgt gctgcgaagg   23520
gcggcgaagc cctgttcgac gccttctccc aggccctgat ccggcgcaac ctgatcggcc   23580
gcatcgcctt gaccggcacc ggctgcctgg ggccctgcca ggccggcgcc aatgtgctga   23640
tctacccggg cgcattgatg tacagctggg tggagccggc ggatgtcgac agcatcctca   23700
cgcatctgct cgaaggcgag cccttcgccg acaagctcac ccccgcggag ctctggtgag   23760
gcatgggtga agtgctgttg ctggagcccg aacgggcgtt cttttccgac cgcacgccga   23820
ccgggctgcg ctacctgctg aacagcgcgc gcggcctcga gcatccggcg gcggtcgaag   23880
ccctgctgct ggaggcccgg cagcgctgga gcgaggagcc ggacgcgcat gtcggcctgt   23940
acaagttcta ctttctccag gcccgctacg cggaggccga agccgccgta tgggaagccc   24000
tgcggcgggc cgcggcctgt gccggcttca gccgcaacta ccggcgcctg caccctgcca   24060
gcgccgactg gcagacacgc cgcggtgcca cgcggttgta cctgttcagc ctcaaggcgc   24120
tgggcgtgat ccgcctgcgc cgtggcaagg tggacaacgc gcggcgggtg ctggagaagc   24180
tgctggagct cgatccgggc aacgagatcg gcggcgaggc gttcctgcag atcgcccgcg   24240
ccttcgagga ggaaaactga tggcggcatc gttcgaagca cgcctgcagg cggcgcggcc   24300
gctgttcggc gaaatccagc gcgcgctgca ggattgcctg cagcgttcgg ccatccgcct   24360
gcaactgccc gacgagcgtg aaccgtcgcg cagcgaagtg cgggtcgacc cgttcgatcg   24420
cagcgaatgc ttctacagcg aatggcgcag cgcccaggcc gatttcctcg gcagcatgca   24480
gatcaacggc gacggtcagg tctatgccga gttcgacgtg ctgctgaagc acccgcacga   24540
gccggcctgg ctggtggagg cggtcgccgc ctggggttgg ccgggggcgc tgaaaagcga   24600
gttgcgcctg ctgccggcgc tcgatcatga atgagctcta cgactggctg ctggccagcg   24660
ccgcgcaggc gcggaccgtc gaacatctgt gcctggggtt gaactggaca ctggccgaag   24720
tcgacggcaa ccagggcttc gccttcagcc cgcgccaggt gccgcgcacg ctcggctggt   24780
cgggcacact cgccggccag ggcaacgccg cgctgctgcc ctggctgctg tcgtggaaca   24840
gcgccgaagc cgcggtcggc ctggccgtgc tcaatgccag cgtgaacacg cggcgggct   24900 gccagcgcga ggcgcaggca ctgcgcacgc aggcaccggg gcatctgcag gtgttcgcac   24960
atttccgtcc acggctggcg ggccagcggg tcgtggtgat cggccattat cccggcctcg   25020
aacggctctg gcaggaccag ccctaccagt gcctggagcg ccagcagcag gagggcgacc   25080
tgcccgattg cgccgccgag tacctgctgc ccgaggccga ctgggtgttc gtcagcgcga   25140
gcagcatcgc caacaagacc ttgccgcgcc tgctcgagct gtcgcgccag gcccaggtgg   25200
tgctgatggg gccgagcctg ccctggctgg acgttggcg gcgcttcggc gtggactacc   25260
tggccggggt tcgcgtgctc gacccggacg gcgtgcggcg ggtgattgcc gagggtggcg   25320
gtacgcggct gttcgccggg ccggtggagt atgccttgat ggcgctcggg aaatgatggg   25380
gtctcacggc cggctgggct ggcggatgct gatctgtcac aagcaccgg tcagcgcgcg   25440 cctgcatttc ctcgtgccgc agcgcggcgg ggtggtcttg ccgcagcccc ttccggccct   25500
```

```
cgcggtattc gccgaaccgc cgatgcaggg cgatctgctg gtccatcctg cgggcgctct   25560
gcgcagcctg cagcgcgacc tggggatcga gaaaccgctg gagctggtgg ccgattaccg   25620
ggtcggcctc gaagtgtcgg gcggggttct gccggtattc ctcgccgcac tggacgggca   25680
cgatcggtgc cgggcggcca tcggaaccca ctggatcgaa ctgacgcaga gcatcggcat   25740
gccctggctg gaccgcgaac tgctcaggcg ggcctatgaa gtgctgatcg ggtgaagcgt   25800
aggcgcgtgg atcgggcggt cgcctagcct gaatttccag acatatggac gccacccatc   25860
ctactgcacc gaaaagcatc gccccgaggg cgggccccccc acaaaagcag ccagcagcac   25920
cgagcccccc gtgggcgcgc cctcgcggtg atgcaggccg gtaggcctgc caaagactga   25980
aaagcatcgc cccgagggcg ggcctcccac aaaagcagcc agcagcaccg agccccgtg    26040 ggcgcgctct cgcggcgatg caggccgta ggcctgccaa agactgaaaa gcatcgcccc    26100
ggggtcgggc ctccacaaag cagtcccgta gggtgggccg ggtggcgttc cgcttcagcc   26160
cacccattcc aggcaatggg cgtcatcgaa gtgggctgaa gcccaccctg ctgctgcgtg   26220
ccgaaatgta acctcgtgac ggatgcgcgg accgatggct gacgtgttgg cgctcagcca   26280
cctcccgcac ctcaggcgcg cagcagcgcc ttggccatct tcggcgacag ctgggcttcg   26340
ctgaactgtg gctcgttcgg cggatagagc aggtcctcga tgatgctgta gccgtgttcc   26400
ttgccgaggg cgatcacgtc gcggacctt tcacaggcct tgagtttttc gccgagcgcc    26460
gggtcgttca gggcttggtt cgagaaggct tggatttcct tgatggacat agggttctct   26520
ctgttgcgat gactggaacc agcgccgaac ggctggcgag gcatgccata gcaacatcga   26580
tgcctgagat cattccattg aatatcaatg gcttatgagg ttttgacgag ctgccgattg   26640
tcgtattggc gacaatcgga caacagccgg gctcaaccca gcagggccac ggccttgatc   26700
tgtgcccaca gcggcagccc gggagcgatg cccaactggt cggccgagcg gcgagtgatg   26760
cgcgccagca gcggcgtgcc gccggcatcc aggcgcacca gcacgtgggc cggggtatct   26820
gccgcggcca gcgcttcgac tcgcgccggc agcaggttgg tgatgctgct gccctcggca   26880
cgggtcagcg ccaggctgac gtcgcgggca tgcacgcgaa agcgcaggcg ctggccgagc   26940
gcttccggcc gctgcgccac cagtacctcg ccgccgggga aggtcaggcg ggtcagatgg   27000
taggcgtcgt cgtgttcggc cacgtgggat tcgaccacca cgccggcgtc ctcgccgagg   27060
gcggtgggca ggtccagtcg tgccagggtt tcgcgcaggc cgccggcggc taccgcccgg   27120
ccctggtcga gcaacaccac gtgatcggcc agccgcgcca cttcgtccgg cgaatggctg   27180
acgtagagca gcgggatgtc gagttcgtcg tgcaggcgtt ccagatagg caggatttcg    27240 ttcttgcgct tgaggtccag cgccgccagc ggttcgtcca tcagcagcag gcgcgggctg   27300
gtgagcaggg cgcgggcgat gccgacgcgc tggcgctcac ccccggacag cgttcccggc   27360
aggcgctcca gcaggtggtc gatacccagc aggttcacca catggtccca gtccacccgg   27420
cgctgggcgg ccttgacccg acgcaggccg tattcgaggt tgcgccgtgc cgtgaggtgc   27480
gggaacaggc tggcttcctg gaatacataa cccagggcgc gcgcgtgcgt cgggacgaac   27540
agcccgcgcg cactgtcctg ccagcgttcg ccgttgactt ccaggtacgc ctcgccggcg   27600
cgctccaggc cggcgacgca gcgcaggcag gtggtcttgc ccgagcccga atggccgaac   27660
agcgccgtca cgccgcgcc aggcagggcg aggtcgacgt ccagttcgaa gccgggccag    27720
gtcaggcgga agcgggcgtg gatctgcccg gcggttggtg agtcgttcat gcacgagtcc   27780
cttcaattga ggccggactt gaaacggcgg ctggagtaca gcgccagcag cacgcagaag   27840
```

| | |
|---|---:|
| gagaacgcca gcatgccgcc ggccagccag tgggcctggg cgtactccat ggcctcgacg | 27900 |
| tggtcgaaga tctgtaccga gaccgtgcgg gtgacaccgg ggatgttgcc gccgatcatc | 27960 |
| aacaccacgc cgaactcgcc gacggtatgg gcgaagccga ggatcgaggc ggtgacgaag | 28020 |
| cccggccgcg ccagcggcag taccacgctg aagaaggtgt cccagggact ggcgcgcagg | 28080 |
| gtggcggcta cttccagcgg gcgctcaccg atggcttcga aggcgttctg caggggttgc | 28140 |
| acgacgaagg gcatggagta aagcaccgag cccaccacca gaccggcgaa ggtaaagggc | 28200 |
| agcagaccga ggccgaggct ctgggtcagc tggccaacca ggccgttagg gcccatggcg | 28260 |
| gtgagcagat agaagcccag cacggtcggc ggcaacacca gtggcagtgc caccactgcg | 28320 |
| ccgaccggcc ccttgagcgg cgaatgagta cgcgccagcc accatgccag cggcgtgccg | 28380 |
| atcagcaaca gcagtgcggt ggtgaggctg ccagcttga aggtcagcca gatagctgcg | 28440 |
| aaatcgacgc tgtcgagcat catcgcggtt cagtccagct catagccgta ggcgcgaatc | 28500 |
| agcgcggcgg cggtatcgcc cctgaggtag tcgagcagcg cctgtgccgc cgggttgccc | 28560 |
| tcgccatggc gaagcagcag ggcgtcctgg cggatcgccg cgtgctggtc ggccggcacc | 28620 |
| acccaggccg agccgcgggc gatgcggccg tcctcggtca cctgggacag cgcgacgaag | 28680 |
| cccagctcgg cattgccgct ggcgacgaac tggtgggcct gggcaatgtt ctcgccctgc | 28740 |
| acgaagcgtg gctgcagccg ttcgcgcagg cccaggcggt ctaaggtttc cagtgccgcg | 28800 |
| gcgccgtagg gggcggtttt gggattggcc agggccaggt gacggaagtc gccgtcggcg | 28860 |
| aggatgcgcc cctgcggatc gacataaccc tcgcgcgccg accacagcac caggctgccg | 28920 |
| atggcatagg tgaagcggct accggagacg ccggaaccct cgtcctcgag tcgtgccggt | 28980 |
| gtgctgtcgt cggccgccag caggatgtcg aagggcgcgc cattgttgat ttgcgcgtag | 29040 |
| aacttgccgg tggcgccgaa ggccagcacg gcgcggtggc cggtgtcgcg ggcgaaggcg | 29100 |
| gcggcgattt tctgcattgg cgcggtgaag ttggccgcca cggccacctg cacgtcgtcg | 29160 |
| gcgatggcgg ttagtggcag gcagagcagc agggcggcgc agaaacggcg gacagaatgc | 29220 |
| atggcgactc cttcaatcg acggcgatga tgacgtggga tgccttgatc agcgcggtgc | 29280 |
| agggctggcc cagggccagg ccgagctctt cggcgctctc gttggtgatc acggcgctga | 29340 |
| gggtgcggtt gcccggcagc agcagcttga cctcgcagtt caccgcgccc ggcatcagcg | 29400 |
| cgctgatggt gccggtgagg cgattgcggg cgctgatctt cacgtcagga tcgggcgaga | 29460 |
| gcagcacgaa gctggccttg atcagcgcca tggcggtatt gctgggcgcc aactgcagtt | 29520 |
| cgtcgatgct gtcgttggtc agcgtggcgc tgatgcacag gcctgcgccg atgtccaggc | 29580 |
| gcaggctgcc gttgacggcc cccttgtcga cggcggtgat acggccgcgg aattgattgc | 29640 |
| gtgcgctggt cttcatggcg atggccctca gcagccggtc gatgtcgtcg aagccttcga | 29700 |
| tgccctcggc gacctgggcg agaaagcgct cgtattcggc ctgcatgcgc cgccatacgt | 29760 |
| ggagcatctc gcggccgaag tcggtcaggc gcgtgccgcc gccctgggcg ccgccggcag | 29820 |
| agcagatcac caacggccgc tcggacaggt tgttcatggc atccactgca tcccaggcgg | 29880 |
| ccttgtagct cagcttgatg gccttggcgg cgcggctgat ggaaccggtg gcctcgatct | 29940 |
| gctccagcag gtcgatgcgc ttgccgccca gatagccttt ctcgcccggg ttgaaccaga | 30000 |
| gctggccgtc gatgcgcagg ggtaggtccg cttcgttcat gtcgtttcct cgggctccgg | 30060 |
| ctctgggcct ggagcaagca agaatgcatc caggtctgtg ttttcaaata aatccatgaa | 30120 |
| aatcaaaaag ttaatgcttt catggaggcc ccgtgagctg tctggaagat gacattgtgt | 30180 |
| gatgcgctat atcgttttgt atatagcgct acagaggtat tccggcccgc ccgaggaacc | 30240 |

```
gcggcctggt gtgtcgcaaa gccgacattg cgccccatgc gtaccgttcg cgacagcggg   30300
aaggtcgtgc gatgaatcta tatgtatttg aaaaataatt gttttcagc ttggcaaggc    30360 tgggcatggg cgttgcagaa gtacctgtgc cgggtggcca gatcgccgcc acagccgagg   30420
agacatgccg atgattaccc tgactgaaag cgccaagagt gcgattaacc gcttcatcag   30480
caacgccgac aaacccaccg ccggcttgcg catccgcgtc gagggcggcg gctgtgcggg   30540
gctgaagtac agcctgaagc tggaagagca aggcctcgac ggggaccagc aggtcgactg   30600
cggcgccttc accgtgctga tcgacgacgc cagcgcaccg ctgctcgacg gcgtgaccat   30660
ggacttcgtc gacagcatgg aaggcagcgg cttcaccttc gtcaacccga acgccagcag   30720
cggttgcagc tgcggcaagt ccttcgcctg ctaagcgcca ttcgaggcgg ccggccacga   30780
ccggccaccc agcattcacc gggagatcag ccgtcatgtg ggattattcg aaaaggtca   30840 aagaacactt ctacaacccg aagaacgccg cgccgtggc cgaggccaat gccgtcggtg    30900
acgtcggctc gctgagctgc ggcgatgccc tgccggctgtc gctgaaggtc gatccggaca   30960
ccgacgtgat tctcgacgcc ggcttccaga ccttcggctg cggctcggca atcgcatcga   31020
gctcggcgct gaccgagatg atcaaggggc tgaccgtcga cgaggcgctg aagatcagca   31080
accaggacat cgccgacttc ctcgacgccg tgccgccgga aagatgcac tgttcggtga    31140 tgggtcgcga ggccttgcag gcggcggtgg ccaactaccg cggcgaaacc ctcgaggacg   31200
accacgagga aggcgcgctg gtgtgcaagt gcttcgccat cgacgaggtg atggtgcgcg   31260
agaccatccg cgccaaccgg ctctccagcg tcgaggacgt gaccaactac accaaggccg   31320
gcggcggttg ctcgtcctgc cacgaaggca tcgagcggtt gctggtcgag gaactggccg   31380
cgcgcggcga gatcttcgtt ccggccggta ccggcgccaa ggcggcgaag aaggccaagg   31440
cgccgctggt gaccctggaa acccgccgg cggctccgca ggcggcgccc accgcgccgc    31500
gcatgaccac cctgcagcgc atccgccgca tcgaacgcgt gctcgaatcg atccgcccga   31560
ccctgcagcg cgaccacggc gacgtcgagc tgctggatgt cgagggcaag aacatctacg   31620
tcaagctgac cggcgcctgc accggctgcc agatggccag catgacgttg tccggcatcc   31680
agcagcggct gatcgaggaa ctcggcgagt tcgtcaaggt ggtcccggtc agctccccgg   31740
cccacagcgc gatggcggag gtgtgagatg agcggcatct atctcgacaa caacgcgacc   31800
acccgtgtcg atgacgaagt ggtgcaggcc atgctgccgt tcttcaccga gcagttcggc   31860 aaccctcgt cgatgcacag cttcggcaac caagtcggca tggcgctgaa gaaggcgcgg    31920
cagagcgtgc agcggctgct cggtgccgag tacgactcgg aaatcgtgtt cacctcctgc   31980
ggcaccgagg ccgattccac cgcgatcctc tcggcgctca aggcccagcc cgagcgcaag   32040
acgatcatca ccacggtggt cgagcacccg gcgatcctca gcctgtgcga ctacctggcc   32100
gaggacggct acaccgtgca caagctcaag gtggacaaga agggccgcct ggatctggac   32160
gagtacgccg cgctgctcga cgacgacgtg gccatcgtct cggtgatgtg ggccaacaac   32220
gagaccggca cgctgttccc ggtggagcag atggcgcaga tggccgacga tgccggggtc   32280
atgttccata gcgatgcggt gcaggcggtc ggcaaggtgc cgatgaacct caagggcagc   32340
gccatccaca tgctctcgct gtccggccac aagctgcatg cgcccaaggg cgtcggggtg   32400
ctctacctgc gccgcggcac gcgcttccgg ccgttgctgc gcggtggcca ccaggagcgc   32460
```

-continued

```
gggcgccgcg ccggcaccga gaacgcggcc tcgatcatcg gcctgggggt cgccgccgag    32520
cgcgcgctgg ccttcatgga acacgagaac accgaggtcc gccgcctgcg cgacaagctc    32580
gaggccggca ttctcgccgc cgtgccctac gccttcgtca ccggcgatcc gggcaatcgc    32640
ctgccgaaca ccgccaacat cgccttcgaa tacatcgagg gcgaggccat cctgctgctg    32700
ctgaacaagg tcggcatcgc cgcctccagc ggttcggcat gcacctctgg gtcgcttgag    32760
ccgtcccacg ttatgcgtgc gatggacatt ccctatacgg cggcccacgg cagcgtgcgc    32820
ttctcgctgt cgcgctacac caccgaggag cagatcgact acgtgatccg cgaggtgccg    32880
ccgatcatcg cccagttgcg caagctgtcg ccctactgga gtggcaacgg cccggccgag    32940
gcagtgggcg actcgttcga accggtctac gcctgaccgc cgcttgaccg cggccccatc    33000
gccgaggagg ttcagcatgt ctatcgtgat cgacgacacc accctgcgtg acggcgaaca    33060
gagcgccggg gtcgccttca gcgccgagga gaagctcgcc atcgcccgtg ctctggcaca    33120
gctcggcgtg ccggagctgg agatcggcat tcccagcatg ggcgaggagg agtgcgaggt    33180
gatgcgcgcc atcgccgggc tggccctgcc ggtgcggctt ctggcctggt gccggttgtg    33240
cgacgctgac ctgctggccg ccggcggcac cggcgtcggc atggtcgacc tgtcgctacc    33300
ggtctcggac ctgatgctgc agcacaagct tggccgcgac cgcgactggg cgttgcgcga    33360
ggccgcgcga ctggtgggcg ctgcgcgcga cgccggcctg gaggtgtgcc tgggctgcga    33420
ggacgcctcg cgcgccgatc cggagttcat cgtccgcgtg gcggaagtcg cccaggccgc    33480
cggtgcgcga cggctgcgct tcgccgatac ggtgggagta atggagccat cgcgatgca    33540 cgcgcgcttc cgctttctcg ccgagcgcct ggatctggag ctggaagtgc acgcccacga    33600
cgacttcggc ctggccacag ccaacaccct ggcagccgtg cgcggaggtg ccacgcatat    33660
caacaccacg gtcaacggcc tcggcgagcg cgccggtaat gccgcgctgg aggaatgcgc    33720
gctggcgctc aagcacctcc acggcatcga ctgcggtatc gacgtgcgcg gcattccctc    33780
gatctcggcg ctggtggagc aggcctccgg gcgccaggtg gcctggcaga agagcgtggt    33840
cggcgccggg gtgttcaccc acgaggcggg tatccatgtc gacgggctgc tcaagcaccg    33900
gcgcaactac gaggggctca accccgacga gctcggcgc agccacagcc tggtgctggg    33960
caagcattcc ggcgcgcaca tggttgagct gagctaccgc gagctgggta tcgagctgca    34020
gcagtggcag agccgcgcgc tgctcggctg catccgccgt ttttccacgc agaccaagcg    34080
cagtcctcag agcgccgacc tgcagggttt ctaccagcag ctgtgcgaac agggcctggc    34140
cctggccgga ggtgccgcat gagcctgtac cgagaatgcc gcgacgacgt ccgttgcgtg    34200
ttccagcgcg accccgcggc gcgctccacg ctggaggtgc tgaccaccta tccgggcgtg    34260
cacgcaatca tgctctaccg cttcgcgcat cgcctgtggc gacgcgagtg gcgctatgcc    34320
gcgcgtctgt tgagtttcgc cggacggctg ctgagcaacg tcgatatcca ccccggcgcc    34380
cgcatcggtg cgcgcttctt cattgaccat ggcgctgggg tggtgatcgg cgaaaccgcc    34440
gagatcggcg acgacgtcac cctctatcac ggtgtgaccc tgggcggaac cagctggcgc    34500
aagggcaagc gccacccgac cctgggcgac ggcgtgctgg tcggcgccgg ggcgaagatc    34560
ctcgggccga tcagcatcgg tgctaatgcc cgggttggcg ccaactcagt ggtggtgcag    34620
aacgtgccgg acgggtgcac ggtggtcggt atccccggca aggtggtgcg cctgcgcgag    34680 gccgccggc ccaacgtgta tggcatcgat ctcgaccatt acctgattcc cgacccggtg    34740
ggcaaggcca tcgcctgtct gctggagcgc ctggacaacc tggaaaggca ggtcgagcag    34800
```

```
ggcggcctgg tcgccgccgg cagccagcag cggcgctacc aggaatgcca gccggacaac    34860
agcctgtgtg aaaacgattg tccggccatg gccgggcgct gacggagcac gcccatggac    34920
ctgcagaatt tcgacggcgc cggcctgtat ttcgacgagc cgcgccagcc gcgcgtcgcg    34980
gcgctgctgg acgaggcgtc ggcgcagtac gccaccggca ctgcggagca gccgctgctg    35040
gcggcgcagg cgctggcgcc gggcgatctc agcgtgctgg tcgggctcta tcgcttctac    35100
ttctaccagc atcgtcatgc cgatgccctg gccatcgccg cgcaggtcct gcaggtggtc    35160
gcgccgcgcc tggggctgcc ctgtgactgg cgtgcgctcg ataccgactg cctggcacgc    35220
gtggcgcccg cgccatcgg cctgctgcgt tttcatctgc tggcgctcaa gggcgccggt    35280
tacctgagcc tgcgcctggg cctgttcggc gagggcaagg cgatgctgag caaggtcgcc    35340
gagctcgatg cggacaatcg cctcggcgcg cgcctgctgc tcgatgtttt ggcggccaac    35400
agcgccgcca ttttcacctt tccccctgct gccaccgtgg agacacgccc atgagcgaac    35460
aagccgccga accgaacctg gacgggccct tggacgaggc gctggaagag ctggtatcgg    35520
ccgaggattt cctgaacttc ttcggcgtgc ccttcgtgcc gtcggtggtg caggtcaacc    35580
gcctgcacat catgcagcgc tatcacgact acctgtgtca ggccggcgat atcgagcacc    35640
tgcaggatgc cgtgcggtac gcggtgtatc gcaagctgct ggtacgtgcc tacgaggatt    35700
tcgtcgcctc cgatgcgcag accgaaaagg tcttcaaggt cttccacatg cacgagccgc    35760
agacgacctt cgtgcccatc gatcaactgc tgggctgacc cgcgggaggt gagcgccatg    35820
agtctgccgc tctacgaata tggccaggcc gtcaggctga tccgcaacgt acgcaacgac    35880
ggcacctacc ccggcaagga caccggcgcc ctgctgatgc cgcgcggcgc ggtgggttgc    35940
gtctacgacg tcggcaccta cctgcaggat cagctgatct accgcgtgca tttcctcgat    36000
cagggctgca cggtgggctg ccgcgaggag gagctgattc ccgcgtcgga cccttggata    36060
cccaacctgt tcgagttccg cgaccaggtg gtcgccaccc gcagcctggc cgtgcgcggc    36120
gaggtggtgg tggagcaggg ccgcaccggc agcatcgaga aggtgctgcg cgacctgccc    36180
ggcggcatcc agtaccacgt ctatttcggc gacggccggg tgcttcaggt gcccgagacg    36240
agcctggcct gggccgacgc gcaggcggga gacgagcatg agcattgatc tggtcatcgg    36300
caaggatgcc cgctaccagc tgctgaaggt cgcccacgag cgtttcggct gtgccccggc    36360
cgccctcagt tcgcaacagc gtgaacaggc cgagcgcatc atcggtcgcc agctgcagct    36420
ggagaacgcc gtgctgcaca cgccgaggc ctgcggtgtg gtgatcccgg acgagcaggt    36480
cgccgatgcc tgggccgaga tcgccgcccg ctacgaggac ccgctcgcgc tgcacaaggc    36540
gctagacgac agtggtctgg acgaagccgg cctgcgccag ctgctggccc gcgaactcaa    36600
ggtcgaaacg gtgctgcagc gtgtctgcgc cgggctgccg gaaatcaccg atacagatgt    36660
cagcctgtac tacttcaatc atccggagcg cttcgtgcgg cccgccacgc gactggcgcg    36720
acagatcctg attaccgtca acgaggattt cccggaaaac agccggacca gcgcttggcg    36780
ccgcatcaac ctgatcgccg agcgcctgct gcgcaagccg cagcgcttcg ccgagcaggc    36840
gctcaagcat tccgagtgcc cttcggcgat ggagggcgga agcctcggcc tgatacgccc    36900
cggcgtgctc tatccgcagc tggaagcctg cctgttcgcc ttgcgcgcag gcgagatcgg    36960
cccggtggtg gagacgccac tgggctttca cctgctgttc tgcgaggaga tccatccggc    37020
gggccatttg tcgctgcagg aggtcttgcc gcacctgcgc gagaagctcc gcgcccgtca    37080
atacgagcgc caccagcgcg catggctggc cggtttgctg cagtccgccc aacctcacc    37140 ggagtcgctg ccatgactga taccgacaag ccctgctgtt cgttctgcgg cgcggaaaaa    37200
```

```
tcaccgacgg tacccttgat cgcgggtaac gaaggccgga tctgcgaggc ctgcgtcaag    37260
ctggcccacc aggtggtgac cagctggggg cagcggcgcc aggcccagca actggcgccg    37320
caactgctca cgccggcggc ctacatgcag catctggacg agtcggtgat cggccaggac    37380
gaggccaagg aaaccctggc ggtggcggtc tacaaccact acctgcgcct gctcaactgc    37440
acccgcgagc cggtctgcca actgggcgga acggtcgagc tggagaagtc caacatcctc    37500
atggccggcc cttcgggcac cggcaagacc ctgctggtgc gcaccctggc gcgcatcctc    37560
ggcgtgccct tcgcctcggc tgatgccacc accctgaccc aggccggcta cgtcggcgac    37620
gacgtcgaca gcatcatcgc ccgcctgctg gaagccgccg gtggcgatgt gcagaaggcg    37680
caatggggca tcgtctatat cgacgaggtg acaagctgg cacggcgtgg cggggcggc     37740
acggcggtgc gcgacatctc cggcgaaggc gtgcagcagg cgctgctcaa gctggtcgag    37800
ggtagcgagg tgcgcatcgg caaggggggc cggcgtggcg aacacggcga ggagcaggtg    37860
gtggatacgc gcaacatcct gttcatcgcc ggtggcgcct ttccgggcct ggaaaccctg    37920
gtcggcagcc gtgtgcatcc gcgtggcagc gcgatcggct tccatgcgcg gccgcagcag    37980
caggcaccgt cgatcaacga gctgctggcg gcgctgctgc cggacgacct ccatgagttc    38040
gggctgatcc ccgagttcat cggtcgcttc ccgatcatca ccttcctccg cgagttggac    38100
cacgcgacgc tgctgcgcat cctcagcgaa ccgcgcaatg cgctggtcaa gcagtaccag    38160
caactgttcg cctaccaggg cgtgaagctg gagttcagcg aggcggcgct cggccacata    38220
gccgaccagg cgctgctgcg ccgcaccggc gcgcgcgggc tgcgcgcggt catggagagc    38280
gcgctgcagc gcaccatgtt cgagatgccg gcgcagccgc agctgcgcag ttgcctgctc    38340
gacctcgacg aggagggccg cgaactggtg gtgctcaggc agttcgacga gtatgccgaa    38400
gcgcaacctg ccgacagccg ggcggccgcg gcgtcctggc agcgttccct gctggtggtg    38460
gatggctagt gtcgcattgc cgacagcggc atgccgctgt cggcggccgg tttgtgtggt    38520
ttgcgacagg taatgttcat gaaaaggctt tgttttcatt ggcttataag aatccagcgg    38580
ctggcgtgtt tcctgctatg agtcttttgc cgagtgggta tgtgggcccg cggtgtttca    38640
ttcatccaaa cagcaatgag gtggcgtgat ggccaggatc ggactttttct tcggcagcaa    38700
cacgggcaag acgcgcaagg tcgccaagat gatcaagaag cgcttcgacg acgacaccct    38760
ggctgatccg ctcaacgtca accgcacgag cgccgcagac ttcgccggct attcgcacct    38820
gatcctcggc acgccgaccc tgggcgaggg cttgctgccg gggctgagcg ccgattgcga    38880
gaacgaaagc tgggaggaat tcctgccgca gatcgagggg ctggatttca ccggcaagac    38940
cgtggccatc ttcggcctcg gcgatcaggt cggctacgcc gacgagtttc tcgatgcgat    39000
gggcgaactg cacgaattct tcagcgagcg cggcgccacc atggtcggcg agtggccgac    39060
cacgggctac gaattcaccc actccgaagc ggtggtggac ggcaagttcg tcgggctggc    39120
gctggacttg gacaaccaga gcaacctcac cgaggagcgg ctgggcgcct ggttgcgaca    39180
gatcgctccg gccttcgaac tgccgctgtg a                                   39211
```

Having thus specifically described and established the nature of the present invention and the way the same should be put into practice, the exclusive right and ownership thereof are hereby asserted and claimed as follows:

1. A method for increasing nitrogen fixation in plants, comprising applying to soil $1.6 \times 10^8$-$4 \times 10^8$ per liter of soil of a recombinant strain of *Pseudomonas fluorescens* that is capable of fixing nitrogen, said recombinant strain comprising the genomic segments PST_1302 to PST_1306 (SEQ ID NO: 5) and PST_1313 to PST_1359 (SEQ ID NO: 6) obtained from *Pseudomonas stutzeri* strain A1501.

2. The method according to claim 1, wherein the plant is a monocotyledon.

3. The method according to claim 1, wherein the plant is a dicotyledon.

4. The method according to claim 3, wherein the plant is selected from the group consisting of *Arabidopsis* and Alfalfa.

5. The method according to claim 2, wherein the plant is Fescue.

6. The method according to claim 1, wherein said genomic segments consist of PST_1302 to PST_1306 (SEQ ID NO: 5) and PST_1313 to PST_1359 (SEQ ID NO: 6).

* * * * *